(12) United States Patent
End

(10) Patent No.: US 6,838,467 B2
(45) Date of Patent: Jan. 4, 2005

(54) DOSING REGIMEN

(75) Inventor: David William End, Ambler, PA (US)

(73) Assignee: Janssen Pharmaceutica N. V., Beerse (BE)

( * ) Notice: Subject to any disclaimer, the term of this patent is extended or adjusted under 35 U.S.C. 154(b) by 0 days.

(21) Appl. No.: 10/220,162

(22) PCT Filed: Feb. 20, 2001

(86) PCT No.: PCT/EP01/01937

§ 371 (c)(1),
(2), (4) Date: Aug. 23, 2002

(87) PCT Pub. No.: WO01/62234

PCT Pub. Date: Aug. 30, 2001

(65) Prior Publication Data

US 2003/0060450 A1 Mar. 27, 2003

Related U.S. Application Data

(60) Provisional application No. 60/184,551, filed on Feb. 24, 2000.

(51) Int. Cl.$^7$ .............................................. A61K 31/47
(52) U.S. Cl. ....................................................... 514/312
(58) Field of Search ............................... 514/301, 311, 514/312

(56) References Cited

U.S. PATENT DOCUMENTS

| | | | | |
|---|---|---|---|---|
| 5,834,434 A | * | 11/1998 | Sebti et al. | .................. 514/19 |
| 5,874,442 A | | 2/1999 | Doll et al. | |

FOREIGN PATENT DOCUMENTS

| | | |
|---|---|---|
| WO | WO 94/10138 A1 | 5/1994 |
| WO | WO 97/16443 A1 | 5/1997 |
| WO | WO 97/21701 A1 | 6/1997 |
| WO | WO 97/30992 A1 | 8/1997 |
| WO | WO 98/28303 A1 | 7/1998 |
| WO | WO 98/40383 A1 | 9/1998 |
| WO | WO 98/49157 A1 | 11/1998 |
| WO | WO 99/45912 A1 | 9/1999 |
| WO | WO 00/01691 A1 | 1/2000 |
| WO | WO 00/12498 A1 | 3/2000 |
| WO | WO 00/12499 A1 | 3/2000 |
| WO | WO 00/39082 A2 | 7/2000 |

OTHER PUBLICATIONS

Parada L. F. et al. "Human EJ bladder carcinoma oncogene is homologue of Harvey sarcoma virus ras gene," *Nature*, 1982, pp. 474–478, vol. 297, No. 5866.

Santos E. et al. "T24 human bladder carcinoma oncogene is an activated form of the normal human homologue of BALB–and Harvey–MSV transforming genes," *Nature*, 1982, pp. 343–347, vol. 298, No. 5872.

Kohl et al., "Selective Inhibition of ras–Dependent Transformation by a Farnesyltransferase Inhibitor," *Science*, 1993, pp. 1934–1937, vol. 260, No. 5116.

* cited by examiner

*Primary Examiner*—Raymond J. Henley, III
(74) *Attorney, Agent, or Firm*—Gabriel Lopez; Alana G. Kriegsman

(57) ABSTRACT

This invention relates to a method of treatment and dosing regimen for treating mammalian tumors by the discontinuous administration of a farnesyl transferase inhibitor over an abbreviated one to five day dosing schedule.

10 Claims, 6 Drawing Sheets

1

DOSING REGIMEN

CROSS REFERENCE TO RELATED APPLICATIONS

This application is a National Stage Application under 35 USC 371 of PCT/EP01/01937 filed Feb. 20, 2001, which claims priority from U.S. Provisional Patent Application Ser. No. 60/184,551, filed Feb. 24, 2000.

FIELD OF THE INVENTION

The present invention relates to a method for treating mammalian tumors by the administration of a farnesyl protein transferase (FPT) inhibitor using an intermittent dosing schedule. The regimen involves the administration of a FPT inhibitor over an abbreviated one to five day dosing schedule whereby anticancer effects are achieved which continue beyond the period of administration.

BACKGROUND OF THE INVENTION

Over the last decade cancer research has identified specific genetic lesions which induce malignant transformation and drive tumor growth. It is now recognized that mutations, deletions or alterations in the expression of normal mammalian genes involved in growth control converts these "protooncogenes" into "oncogenes". The ras family of oncogenes consisting of H-ras, K-ras and N-ras oncogenes encode a highly conserved GTP-binding protein or Mr=21,000 (p21).

Oncogenes frequently encode components of signal transduction pathways which lead to stimulation of cell growth and mitogenesis. Oncogene expression in cultured cells leads to cellullar transformation, characterized by the ability of cells to grow in soft agar and the growth of cells as dense foci lacking the contact inhibition exhibited by non-transformed cells. Mutation and/or overexpression of certain oncogenes is frequently associated with human cancer. In order to acquire transforming potential the precursor of the ras oncoprotein must undergo farnesylation of the cysteine residue located in a carboxyl-terminal tetrapeptide. Inhibitors of the enzyme that catalyzes this modification, farnesyl protein tranferase, have therefore been suggested as anticancer agents for tumors in which ras contributes to transformation. Mutated oncogenic forms of ras are frequently found in many human cancers, most notably in more than 50% of colon and pancreatic carcinomas (Kohl et al., Science, vol. 260, 1384 to 1837, 1993).

The protein products of the ras ocogenes have been the focus of oncology drug discovery efforts because of some unique features of the cellular metabolism of these proteins. To function in signal transduction and cell transformation, ras must attach to the plasma membrane to promote interactions with membrane localization also SH2/SH3 domain adaptor proteins Grb2 and SOS. Ras membrane localization also functions in the activation of downstream effectors such as Raf protein kinase. Newly synthesized Ras proteins must pe posttranslationally modified in mammalian cells by farnesylation followed by the proteolytiac cleavage of the three terminal amino acids and carboxy-O-methylation to produce the hydrophobicity or recognition sites which allow proper membrane localization. The initial and rate-limiting post-translational modification of Ras involves the covalent attachment of farnesol via a thioether linkage to a single cysteine residue positioned four amino acids from the carboxy terminus of the protein. This reaction is catalyzed by farnesyl protein transferase (FPT). The enzyme requires only the four C-terminal amino acids or CAAX motif for specific binding and catalysis of protein substrates.

Farnesyl protein transferase inhibitors have been described as being useful in the treatment of mammalian cancers and in particular in the treatment of colon and pancreatic cancers.

WO-97/21701, and it's United States counterpart, U.S. Pat. No. 6,037,350, describe the preparation, formulation and pharmaceutical properties of farnesyl protein transferase inhibiting (imidazoly-5-yl)methyl-2-quinolinone derivatives of formulas (I), (II) and (III), as well as intermediates of formula (II) and (III) that are metablolized in vivo to the compounds of formula (I). The compounds of formulas (I), (II) and (III) are represented by

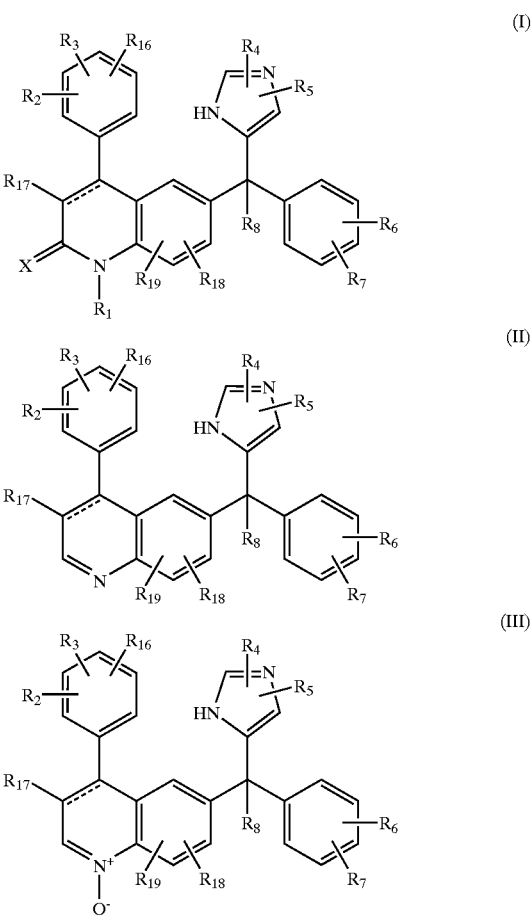

the pharmaceutically acceptable acid or base addition salts and the stereochemically isomeric forms thereof, wherein the dotted line represents an optional bond;

X is oxygen or sulfur;

$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula —Alk$^1$—C(=O)—R$^9$, —Alk$^1$—S(O)-R$^9$ or —Alk$^1$—S(O)$_2$—R$^9$, wherein
  Alk$^1$ is $C_{1-6}$alkanediyl;
  R$^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;

$R^2$, $R^3$ and $R^{16}$ each independently are hydrogen, hydroxy, halo, cyano, $C_{1-6}$alkyl, $C_{1-6}$alkyloxy, hydroxyC$_{1-6}$alkyloxy, C$_{1-6}$alkyloxyC$_{1-6}$alkyloxy, aminoC$_{1-6}$alkyl-oxy, mono- or di(C$_{1-6}$alkyl)aminoC$_{1-6}$alkyloxy, Ar$^1$, Ar$^2$C$_{1-6}$alkyl, Ar$^2$oxy, Ar$^2$C$_{1-6}$alkyloxy, hydroxycarbonyl, C$_{1-6}$alkyloxycarbonyl, trihalomethyl, trihalomethoxy, C$_{2-6}$alkenyl, 4,4-dimethyloxazolyl; or when on adjacent positions R$^2$ and R$^3$ taken together may form a bivalent radical of formula —O—CH$_2$—O— (a-1)

—O—CH$_2$—CH$_2$—O— (a-2)

—O—CH=CH— (a-3)

—O—CH$_2$—CH$_2$— (a-4)

—O—CH$_2$—CH$_2$—CH$_2$— (a-5) or

—CH=CH—CH=CH— (a-6)

R$^4$ and R$^5$ each independently are hydrogen, halo, Ar$^1$, C$_{1-6}$alkyl, hydroxyC$_{1-6}$alkyl, C$_{1-6}$alkyloxyC$_{1-6}$alkyl, C$_{1-6}$alkyloxy, C$_{1-6}$alkylthio, amino, hydroxycarbonyl, C$_{1-6}$alkyloxycarbonyl, C$_{1-6}$alkylS(O)C$_{1-6}$alkyl or C$_{1-6}$alkylS(O)$_2$C$_{1-6}$alkyl;

R$^6$ and R$^7$ each independently are hydrogen, halo, cyano, C$_{1-6}$alkyl, C$_{1-6}$alkyloxy, Ar$^2$oxy, trihalomethyl, C$_{1-6}$alkylthio, di(C$_{1-6}$alkyl)amino, or when on adjacent positions R$^6$ and R$^7$ taken together may form a bivalent radical of formula —O—CH$_2$—O— (c-1) or —CH=CH—CH=CH— (c-2)

R$^8$ is hydrogen, C$_{1-6}$alkyl, cyano, hydroxycarbonyl, C$_{1-6}$alkyloxycarbonyl, C$_{1-6}$alkylcarbonylC$_{1-6}$alkyl, cyanoC$_{1-6}$alkyl, C$_{1-6}$alkyloxycarbonylC$_{1-6}$alkyl, carboxyC$_{1-6}$alkyl, hydroxyC$_{1-6}$alkyl, aminoC$_{1-6}$alkyl, mono- or di(C$_{1-6}$alkyl)-aminoC$_{1-6}$alkyl, imidazolyl, haloC$_{1-6}$alkyl, C$_{1-6}$alkyloxyC$_{1-6}$alkyl, aminocarbonylC$_{1-6}$alkyl, or a radical of formula —O—R$^{10}$ (b-1)

—S—R$^{10}$ (b-2)

—N—R$^{11}$R$^{12}$ (b-3)

wherein R$^{10}$ is hydrogen, C$_{1-6}$alkyl, C$_{1-6}$alkylcarbonyl, Ar$^1$, Ar$^2$C$_{1-6}$alkyl, C$_{1-6}$alkyloxycarbonyl-C$_{1-6}$alkyl, or a radical or formula —Alk$^2$—OR$^{13}$ or —Alk$^2$—NR$^{14}$R$^{15}$;

R$^{11}$ is hydrogen, C$_{1-12}$alkyl, Ar$^1$ or Ar$^2$C$_{1-6}$alkyl;

R$^{12}$ is hydrogen, C$_{1-6}$alkyl, C$_{1-6}$alkylcarbonyl, C$_{1-6}$alkyloxycarbonyl, C$_{1-6}$alkylaminocarbonyl, Ar$^1$, Ar$^2$C$_{1-6}$alkyl, C$_{1-6}$alkylcarbonyl-C$_{1-6}$alkyl, a natural amino acid, Ar$^1$carbonyl, Ar$^2$C$_{1-6}$alkylcarbonyl, aminocarbonylcarbonyl, C$_{1-6}$alkyloxyC$_{1-6}$alkylcarbonyl, hydroxy, C$_{1-6}$alkyloxy, aminocarbonyl, di(C$_{1-6}$alkyl)aminoC$_{1-6}$alkylcarbonyl, amino, C$_{1-6}$alkylamino, C$_{1-6}$alkylcarbonylamino, or a radical or formula —Alk$^2$—OR$^{13}$ or —Alk$^2$—NR$^{14}$R$^{15}$;

wherein Alk$^2$ is C$_{1-6}$alkanediyl;

R$^{13}$ is hydrogen, C$_{1-6}$alkyl, C$_{1-6}$alkylcarbonyl, hydroxy-C$_{1-6}$alkyl, Ar$^1$ or Ar$^2$C$_{1-6}$alkyl;

R$^{14}$ is hydrogen, C$_{1-6}$alkyl, Ar$^1$ or Ar$^2$C$_{1-6}$alkyl;

R$^{15}$ is hydrogen, C$_{1-6}$alkyl, C$_{1-6}$alkylcarbonyl, Ar$^1$ or Ar$^2$C$_{1-6}$alkyl;

R$^{17}$ is hydrogen, halo, cyano, C$_{1-6}$alkyl, C$_{1-6}$alkyloxycarbonyl, Ar$^1$;

R$^{18}$ is hydrogen, C$_{1-6}$alkyl, C$_{1-6}$alkyloxy or halo;

R$^{19}$ is hydrogen or C$_{1-6}$alkyl;

Ar$^1$ is phenyl or phenyl substituted with C$_{1-6}$alkyl, hydroxy, amino, C$_{1-6}$alkyloxy or halo; and Ar$^2$ is phenyl or phenyl substituted with C$_{1-6}$alkyl, hydroxy, amino, C$_{1-6}$alkyloxy or halo.

WO-97/16443, and it's United States counterpart, U.S. Pat. No. 5,968,952, concern the preparation, formulation and pharmaceutical properties of farnesyl protein transferase inhibiting compounds of formula (IV), as well as intermediates of formula (V) and (VI) that are metabolized in vivo to the compounds of formula (IV). The compounds of formulas (IV), (V) and (VI) are represented by

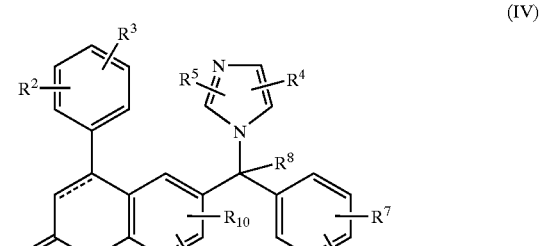

(IV)

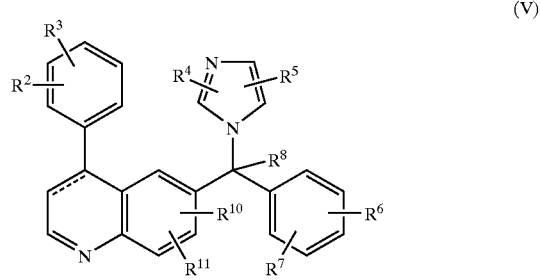

(V)

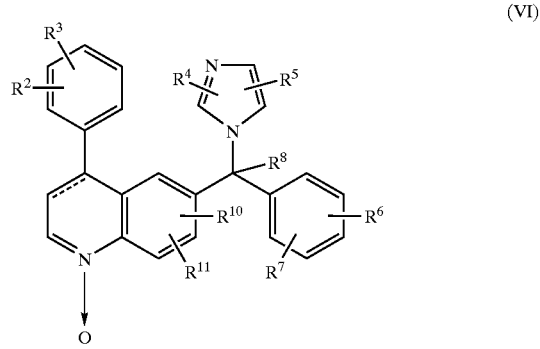

(VI)

the pharmaceutically acceptable acid or base addition salts and the stereochemically isomeric forms thereof, wherein the dotted line represents an optional bond;

X is oxygen or sulfur;

R$^1$ is hydrogen, C$_{1-12}$alkyl, Ar$^1$, Ar$^2$C$_{1-6}$alkyl, quinolinylC$_{1-6}$alkyl, pyridyl-C$_{1-6}$alkyl, hydroxyC$_{1-6}$alkyl, C$_{1-6}$alkyloxyC$_{1-6}$alkyl, mono- or di(C$_{1-6}$alkyl)-aminoC$_{1-6}$alkyl, aminoC$_{1-6}$alkyl, or a radical of formula —Alk$^1$—C(=O)—R$^9$, —Alk$^1$—S(O)—R$^9$ or —Alk$^1$—S(O)$_2$—R$^9$, wherein Alk$^1$ is C$_{1-6}$alkanediyl, R$^9$ is hydroxy, C$_{1-6}$alkyl, C$_{1-6}$alkyloxy, amino, C$_{1-8}$alkylamino or C$_{1-8}$alkylamino substituted with C$_{1-6}$alkyloxycarbonyl;

$R^2$ and $R^3$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino-$C_{1-6}$alkyloxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl; or
when on adjacent positions $R^2$ and $R^3$ taken together may form a bivalent radical of formula

| | |
|---|---|
| —O—CH$_2$—O— | (a-1) |
| —O—CH$_2$—CH$_2$—O— | (a-2) |
| —O—CH=CH— | (a-3) |
| —O—CH$_2$—CH$_2$— | (a-4) |
| —O—CH$_2$—CH$_2$—CH$_2$— | (a-5) | or

| | |
|---|---|
| —CH=CH—CH=CH— | (a-6) |

$R^4$ and $R^5$ each independently are hydrogen, $Ar^1$, $C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2$$C_{1-6}$alkyl;

$R^6$ and $R^7$ each independently are hydrogen, halo, cyano, $C_{1-6}$alkyl, $C_{1-6}$alkyloxy or $Ar^2$oxy;

$R^8$ is hydrogen, $C_{1-6}$alkyl, cyano, hydroxycarbonyl, $C_{1-6}$alkyloxycarbonyl, $C_{1-6}$alkyl-carbonyl$C_{1-6}$alkyl, cyano$C_{1-6}$alkyl, $C_{1-6}$alkyloxycarbonyl$C_{1-6}$alkyl, hydroxy-carbonyl$C_{1-6}$alkyl, hydroxy$C_{1-6}$alkyl, amino$C_{1-6}$alkyl, mono- or di($C_{1-6}$alkyl)-amino$C_{1-6}$alkyl, halo$C_{1-6}$alkyl, $C_{1-6}$alkyloxy$C_{1-6}$alkyl, aminocarbonyl$C_{1-6}$alkyl, $Ar^1$, $Ar^2C_{1-6}$alkyloxy$C_{1-6}$alkyl, $C_{1-6}$alkylthio$C_{1-6}$alkyl;

$R^{10}$ is hydrogen, $C_{1-6}$alkyl, $C_{1-6}$alkyloxy or halo;

$R^{11}$ is hydrogen or $C_{1-6}$alkyl;

$Ar^1$ is phenyl or phenyl substituted with $C_{1-6}$alkyl, hydroxy, amino, $C_{1-6}$alkyloxy or halo;

$Ar^2$ is phenyl or phenyl substituted with $C_{1-6}$alkyl, hydroxy, amino, $C_{1-6}$alkyloxy or halo.

WO-98/40383, and it's United States counterpart, U.S. Pat. No. 6,187,786, concern the preparation, formulation and pharmaceutical properties of farnesyl protein transferase inhibiting compounds of formula (VII)

(VII)

the pharmaceutically acceptable acid addition salts and the stereochemically isomeric forms thereof, wherein
the dotted line represents an optional bond;
X is oxygen or sulfur;

—A— is a bivalent radical of formula

| | | | |
|---|---|---|---|
| —CH=CH— | (a-1), | —CH$_2$—S— | (a-6), |
| —CH$_2$—CH$_2$— | (a-2), | —CH$_2$—CH$_2$—S— | (a-7), |
| —CH$_2$—CH$_2$—CH$_2$— | (a-3), | —CH=N— | (a-8), |
| —CH$_2$—O— | (a-4), | —N=N— | (a-9), or |
| —CH$_2$—CH$_2$—O— | (a-5), | —CO—NH— | (a-10); | wherein optionally one hydrogen atom may be replaced by $C_{1-4}$alkyl or $Ar^1$;

$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino$C_{1-6}$alkyloxy, $Ar^2$, $Ar^2$-$C_{1-6}$alkyl, $Ar^2$-oxy, $Ar^2$—$C_{1-6}$alkyloxy; or when on adjacent positions $R^1$ and $R^2$ taken together may form a bivalent radical of formula

| | |
|---|---|
| —O—CH$_2$—O— | (b-1) |
| —O—CH$_2$—CH$_2$—O— | (b-2) |
| —O—CH=CH— | (b-3) |
| —O—CH$_2$—CH$_2$— | (b-4) |
| —O—CH$_2$—CH$_2$—CH$_2$— | (b-5) | or

| | |
|---|---|
| —CH=CH—CH=CH— | (b-6) |

$R^3$ and $R^4$ each independently are hydrogen, halo, cyano, $C_{1-6}$alkyl, $C_{1-6}$alkyloxy, $Ar^3$-oxy, $C_{-6}$alkylthio, di($C_{1-6}$alkyl)amino, trihalomethyl, trihalomethoxy, or when on adjacent positions $R^3$ and $R^4$ taken together may form a bivalent radical of formula

| | |
|---|---|
| —O—CH$_2$—O— | (c-1) |
| —O—CH$_2$—CH$_2$—O— | (c-2) | or

| | |
|---|---|
| —CH=CH—CH=CH— | (c-3) |

$R^5$ is a radical of formula (d-1)

(d-2)

wherein $R^{13}$ is hydrogen, halo, $Ar^4$, $C_{1-6}$alkyl, hydroxy$C_{1-6}$alkyl, $C_{1-6}$alkyloxy-$C_{1-6}$alkyl, $C_{1-6}$alkyloxy, $C_{1-6}$alkylthio, amino, $C_{1-6}$alkyloxy-carbonyl, $C_{1-6}$alkylS(O)$C_{1-6}$alkyl or $C_{1-6}$alkylS(O)$_2$$C_{1-6}$alkyl;

$R^{14}$ is hydrogen, $C_{1-6}$alkyl or di($C_{1-4}$alkyl)aminosulfonyl;

$R^6$ is hydrogen, hydroxy, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl$C_{1-6}$alkyl, $C_{1-6}$alkyloxycarbonyl$C_{1-6}$alkyl, $C_{1-6}$alkylcarbonyl-$C_{1-6}$alkyl, $C_{1-6}$alkyloxycarbonyl, mono- or di($C_{1-6}$alkyl)amino$C_{1-6}$alkyl, $Ar^5$, $Ar^5$—$C_{1-6}$alkyloxy$C_{1-6}$alkyl; or a radical of formula —O—$R^7$ (e-1)

—S—$R^7$ (e-2)

—N—$R^8R^9$ (e-3)

wherein $R^7$ is hydrogen, $C_{1-6}$alkyl, $C_{1-6}$alkylcarbonyl, $Ar^6$, $Ar^6$—$C_{1-6}$alkyl, $C_{1-6}$alkyloxycarbonyl$C_{1-6}$alkyl, or a radical of formula —Alk—$OR^{10}$ or —Alk—$NR^{11}R^{12}$;

$R^8$ is hydrogen, $C_{1-6}$alkyl, $Ar^7$ or $Ar^7$—$C_{1-6}$alkyl;

$R^9$ is hydrogen, $C_{1-6}$alkyl, $C_{1-6}$alkylcarbonyl, $C_{1-6}$alkyloxycarbonyl, $C_{1-6}$alkylaminocarbonyl, $Ar^8$, $Ar^8$—$C_{1-6}$alkyl, $C_{1-6}$alkylcarbonyl-$C_{1-6}$alkyl, $Ar^8$-carbonyl, $Ar^8$-$C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula —Alk—$OR^{10}$ or —Alk—$NR^{11}R^{12}$;

wherein Alk is $C_{1-6}$alkanediyl;

$R^{10}$ is hydrogen, $C_{1-6}$alkyl, $C_{1-6}$alkylcarbonyl, hydroxy-$C_{1-6}$alkyl, $Ar^9$ or $Ar^9$—$C_{1-6}$alkyl;

$R^{11}$ is hydrogen, $C_{1-6}$alkyl, $C_{1-6}$alkylcarbonyl, $Ar^{10}$ or $Ar^{10}$—$C_{1-6}$alkyl;

$R^{12}$ is hydrogen, $C_{1-6}$alkyl, $Ar^{11}$ or $Ar^{11}$—$C_{1-6}$alkyl; and $Ar^1$ to $Ar^{11}$ are each independently selected from phenyl; or phenyl substituted with halo, $C_{1-6}$alkyl, $C_{1-6}$alkyloxy or trifluoromethyl.

WO-98/49157 and it's United States counterpart, U.S. Pat. No. 6,177,432, concern the preparation, formulation and pharmaceutical properties of farnesyl protein transferase inhibiting compounds of formula (VIII).

(VIII)

the pharmaceutically acceptable acid addition salts and the stereochemically isomeric forms thereof, wherein the dotted line represents an optional bond;

X is oxygen or sulfur;

$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino$C_{1-6}$alkyloxy, $Ar^1$, $Ar^1C_{1-6}$alkyl, $Ar^1$oxy or $Ar^1C_{1-6}$alkyloxy;

$R^3$ and $R^4$ each independently are hydrogen, halo, cyano, $C_{1-6}$alkyl, $C_{1-6}$alkyloxy, $Ar^1$oxy, $C_{1-6}$alkylthio, di($C_{1-6}$alkyl)amino, trihalomethyl or trihalomethoxy;

$R^5$ is hydrogen, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl$C_{1-6}$alkyl, $C_{1-6}$alkyloxycarbonyl$C_{1-6}$alkyl, $C_{1-6}$alkylcarbonyl-$C_{1-6}$alkyl, $C_{1-6}$alkyloxycarbonyl, mono- or di($C_{1-6}$alkyl)amino$C_{1-6}$alkyl, $Ar^1$, $Ar^1C_{1-6}$alkyloxy$C_{1-6}$alkyl; or a radical of formula —O—$R^{10}$ (a-1)

—S—$R^{10}$ (a-2)

—N—$R^{11}R^{12}$ (a-3)

wherein $R^{10}$ is hydrogen, $C_{1-6}$alkyl, $C_{1-6}$alkylcarbonyl, $Ar^1$, $Ar^1C_{1-6}$alkyl, $C_{1-6}$alkyloxycarbonyl$C_{1-6}$alkyl, or a radical of formula —Alk—$OR^{13}$ or —Alk—$NR^{14}R^{15}$;

$R^{11}$ is hydrogen, $C_{1-6}$alkyl, $Ar^1$ or $Ar^1C_{1-6}$alkyl;

$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, $Ar^1$, $Ar^1C_{1-6}$alkyl, $C_{1-6}$alkylcarbonyl-$C_{1-6}$alkyl, $Ar^1$carbonyl, $Ar^1C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula —Alk—$OR^{13}$ or —Alk—$NR^{14}R^{15}$;

wherein Alk is $C_{1-6}$alkanediyl;

$R^{13}$ is hydrogen, $C_{1-6}$alkyl, $C_{1-6}$alkylcarbonyl, hydroxy-$C_{1-6}$alkyl, $Ar^1$ or $Ar^1C_{1-6}$alkyl;

$R^{14}$ is hydrogen, $C_{1-6}$alkyl, $Ar^1$ or $Ar^1C_{1-6}$alkyl;

$R^{15}$ is hydrogen, $C_{1-6}$alkyl, $C_{1-6}$alkylcarbonyl, $Ar^1$ or $Ar^1C_{1-6}$alkyl;

$R^6$ is a radical of formula (b-1)

(b-2)

wherein $R^{16}$ is hydrogen, halo, $Ar^1$, $C_{1-6}$alkyl, hydroxy$C_{1-6}$alkyl, $C_{1-6}$alkyloxy-$C_{1-6}$alkyl, $C_{1-6}$alkyloxy, $C_{1-6}$alkylthio, amino, $C_{1-6}$alkyloxycarbonyl, $C_{1-6}$alkylthio$C_{1-6}$alkyl, $C_{1-6}$alkylS(O)$C_{1-6}$alkyl or $C_{1-6}$alkylS(O)$_2C_{1-6}$alkyl;

$R^{17}$ is hydrogen, $C_{1-6}$alkyl or di($C_{1-4}$alkyl)aminosulfonyl;

$R^7$ is hydrogen or $C_{1-6}$alkyl provided that the dotted line does not represent a bond;

$R^8$ is hydrogen, $C_{1-6}$alkyl or $Ar^2CH_2$ or $Het^1CH_2$;

$R^9$ is hydrogen, $C_{1-6}$alkyl, $C_{1-6}$alkyloxy or halo; or $R^8$ and $R^9$ taken together to form a bivalent radical of formula —CH=CH— (c-1)

—CH$_2$—CH$_2$— (c-2)

—CH$_2$—CH$_2$—CH$_2$—      (c-3)

—CH$_2$—O—      (c-4)

or

—CH$_2$—CH$_2$—O—      (c-5)

Ar$^1$ is phenyl; or phenyl substituted with 1 or 2 substituents each independently selected from halo, C$_{1-6}$alkyl, C$_{1-6}$alkyloxy or trifluoromethyl;

Ar$^2$ is phenyl; or phenyl substituted with 1 or 2 substituents each independently selected from halo, C$_{1-6}$alkyl, C$_{1-6}$alkyloxy or trifluoromethyl; and Het$^1$ is pyridinyl; pyridinyl substituted with 1 or 2 substituents each independently selected from halo, C$_{1-6}$alkyl, C$_{1-6}$alkyloxy or trifluoromethyl.

WO-00/39082, and it's United States counterpart, U.S. patent application Ser. No. 09/868,992, flied Aug. 29, 2001, concern the preparation, formulation and pharmaceutical properties of farnesyl protein transferase inhibiting compounds of formula (IX)

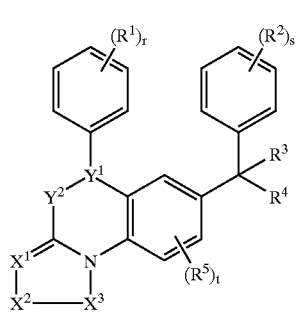

(IX)

or the pharmaceutically acceptable acid addition salts and the stereochemically isomeric forms thereof, wherein =X$^1$—X$^2$—X$^3$— is a trivalent radical of formula

| =N—CR$^6$=CR$^7$— | (x-1), | =CR$^6$—CR$^7$=CR$^8$— | (x-6), |
|---|---|---|---|
| =N—N=CR$^6$— | (x-2), | =CR$^6$—N=CR$^7$— | (x-7), |
| =N—NH—C(=O)— | (x-3), | =CR$^6$—NH—C(=O)— | (x-8), or |
| =N—N=N— | (x-4), | =CR$^6$—N=N— | (x-9); |
| =N—CR$^6$=N— | (x-5), | | | wherein each R$^6$, R$^7$ and R$^8$ are independently hydrogen, C$_{1-4}$alkyl, hydroxy, C$_{1-4}$alkyloxy, aryloxy, C$_{1-4}$alkyloxycarbonyl, hydroxyC$_{1-4}$alkyl, C$_{1-4}$alkyloxyC$_{1-4}$alkyl, mono- or di(C$_{1-4}$alkyl)aminoC$_{1-4}$alkyl, cyano, amino, thio, C$_{1-4}$alkylthio, arylthio or aryl;

>Y$^1$-Y$^2$ is a trivalent radical of formula

>CH—CHR$^9$—      (y-1)

>C=N—      (y-2)

>CH—NR$^9$—      (y-3)

or

>C=CR$^9$—      (y-4)

wherein each R$^9$ independently is hydrogen, halo, halocarbonyl, aminocarbonyl, hydroxyC$_{1-4}$alkyl, cyano, carboxyl, C$_{1-4}$alkyl, C$_{1-4}$alkyloxy, C$_{1-4}$alkyloxyC$_{1-4}$alkyl, C$_{1-4}$alkyloxycarbonyl, mono- or di(C$_{1-4}$alkyl)amino, mono- or di(C$^{1-4}$alkyl)aminoC$_{1-4}$alkyl, aryl;

r and s are each independently 0, 1, 2, 3, 4 or 5;

t is 0, 1, 2 or 3;

each R$^1$ and R$^2$ are independently hydroxy, halo, cyano, C$_{1-6}$alkyl, trihalomethyl, trihalomethoxy, C$_{2-6}$alkenyl, C$_{1-6}$alkyloxy, hydroxyC$_{1-6}$alkyloxy, C$_{1-6}$alkylthio, C$_{1-6}$alkyloxyC$_{1-6}$alkyloxy, C$_{1-6}$alkyloxycarbonyl, aminoC$_{1-6}$alkyloxy, mono- or di(C$_{1-6}$alkyl)amino, mono- or di(C$_{1-6}$alkyl)aminoC$_{1-6}$alkyloxy, aryl, arylC$_{1-6}$alkyl, aryloxy or arylC$_{1-6}$alkyloxy, hydroxycarbonyl, C$_{1-6}$alkyloxycarbonyl, aminocarbonyl, aminoC$_{1-6}$alkyl, mono- or di(C$_{1-6}$alkyl)aminocarbonyl, mono- or di(C$_{1-6}$alkyl)aminoC$_{1-6}$alkyl; or two R$^1$ or R$^2$ substituents adjacent to one another on the phenyl ring may independently form together a bivalent radical of formula —O—CH$_2$—O—      (a-1)

—O—CH$_2$—CH$_2$—O—      (a-2)

—O=CH=CH—      (a-3)

—O—CH$_2$—CH$_2$—      (a-4)

—O—CH$_2$—CH$_2$—CH$_2$—      (a-5)

or

—CH=CH—CH=CH—      (a-6)

R$^3$ is hydrogen, halo, C$_{1-6}$alkyl, cyano, haloC$_{1-6}$alkyl, hydroxyC$_{1-6}$alkyl, cyanoC$_{1-6}$alkyl, aminoC$_{1-6}$alkyl, C$_{1-6}$alkyloxyC$_{1-6}$alkyl, C$_{1-6}$alkylthioC$_{1-6}$alkyl, aminocarbonylC$_{1-6}$alkyl, hydroxycarbonyl, hydroxycarbonylC$_{1-6}$alkyl, C$_{1-6}$alkyloxycarbonylC$_{1-6}$alkyl, C$_{1-6}$alkylcarbonylC$_{1-6}$alkyl, C$_{1-6}$alkyloxycarbonyl, aryl, arylC$_{1-6}$alkyloxyC$_{1-6}$alkyl, mono- or di(C$_{1-6}$alkyl)aminoC$_{1-6}$alkyl;

or a radical of formula

—O—R$^{10}$      (b-1)

—S—R$^{10}$      (b-2)

—NR$^{11}$R$^{12}$      (b-3)

wherein R$^{10}$ is hydrogen, C$_{1-6}$alkyl, C$_{1-6}$alkylcarbonyl, aryl, arylC$_{1-6}$alkyl, C$_{1-6}$alkyloxycarbonylC$_{1-6}$alkyl, or a radical of formula —Alk—OR$^{13}$ or —Alk—NR$^{14}$R$^{15}$;

R$^{11}$ is hydrogen, C$_{1-6}$alkyl, aryl or arylC$_{1-6}$alkyl;

R$^{12}$ is hydrogen, C$_{1-6}$alkyl, aryl, hydroxy, amino, C$_{1-6}$alkyloxy, C$_{1-6}$alkylcarbonylC$_{1-6}$alkyl, arylC$_{1-6}$alkyl, C$_{1-6}$alkylcarbonylamino, mono- or di(C$_{1-6}$alkyl)amino, C$_{1-6}$alkylcarbonyl, aminocarbonyl, arylcarbonyl, haloC$_{1-6}$alkylcarbonyl, arylC$_{1-6}$alkylcarbonyl, C$_{1-6}$alkyloxycarbonyl, C$_{1-6}$alkyloxyC$_{1-6}$alkylcarbonyl, mono- or di(C$_{1-6}$alkyl)aminocarbonyl wherein the alkyl moiety may optionally be substituted by one or more substituents independently selected from aryl or C$_{1-3}$alkyloxycarbonyl, aminocarbonylcarbonyl, mono- or di(C$_{1-6}$alkyl)aminoC$_{1-6}$alkylcarbonyl, or a radical or formula —Alk—OR$^{13}$ or —Alk—NR$^{14}$R$^{15}$;

wherein Alk is C$_{1-6}$alkanediyl;

R$^{13}$ is hydrogen, C$_{1-6}$alkyl, C$_{1-6}$alkylcarbonyl, hydroxyC$_{1-6}$alkyl, aryl or arylC$_{1-6}$alkyl;

R$^{14}$ is hydrogen, C$_{1-6}$alkyl, aryl or arylC$_{1-6}$alkyl;

$R^{15}$ is hydrogen, $C_{1-6}$alkyl, $C_{1-6}$alkylcarbonyl, aryl or aryl$C_{1-6}$alkyl;

$R^4$ is a radical of formula

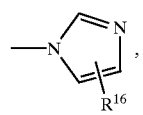 (c-1)

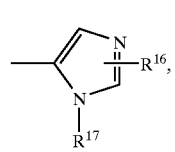 (c-2)

wherein $R^{16}$ is hydrogen, halo, aryl, $C_{1-6}$alkyl, hydroxy$C_{1-6}$alkyl, $C_{1-6}$aikyloxy$C_{1-6}$alkyl, $C_{1-6}$alkyloxy, $C_{1-6}$alkylthio, amino, mono- or di($C_{1-4}$alkyl)amino, hydroxycarbonyl, $C_{1-6}$alkyloxycarbonyl, $C_{1-6}$alkylthio$C_{1-6}$alkyl, $C_{1-6}$alkylS(O)$C_{1-6}$alkyl or $C_{1-6}$alkylS(O)$_2$$C_{1-6}$alkyl;

$R^{16}$ may also be bound to one of the nitrogen atoms in the imidazole ring of formula (c-1) or (c-2), in which case the meaning of $R^{16}$ when bound to the nitrogen is limited to hydrogen, aryl, $C_{1-6}$alkyl, hydroxy$C_{1-6}$alkyl, $C_{1-6}$alkyloxy$C_{1-6}$alkyl, $C_{1-6}$alkyloxycarbonyl, $C_{1-6}$alkylS(O)$C_{1-6}$alkyl or $C_{1-6}$alkylS(O)$_2$$C_{1-6}$alkyl;

$R^{17}$ is hydrogen, $C_{1-6}$alkyl, $C_{1-6}$alkyloxy$C_{1-6}$alkyl, aryl$C_{1-6}$alkyl, trifluoromethyl or di($C_{1-4}$alkyl) aminosulfonyl;

$R^5$ is $C_{1-6}$alkyl , $C_{1-6}$alkyloxy or halo;

aryl is phenyl, naphthalenyl or phenyl substituted with 1 or more substituents each independently selected from halo, $C_{1-6}$alkyl, $C_{1-6}$alkyloxy or trifluoromethyl.

Other useful farnesyl protein transferase inhibitors include Arglabin (i.e.1(R)-10-epoxy-5(S),7(S)-guaia-3(4),11(13)-dien-6,12-olide descibed in WO-98/28303 (NuOncology Labs); perrilyl alcohol described in WO-99/45912 (Wisconsin Genetics); SCH-66336, i.e. (+)-(R)-4-[2-[4-(3,10-dibromo-8-chloro-5,6-dihydro-11H-benzo[5,6]cyclohepta[1,2-b]pyridin-11-yl)piperidin-1-yl]-2-oxoethyl]piperidine-1-carboxamide, described in U.S. Pat. No. 5874442 (Schering); L778123, i.e. 1-(3-chlorophenyl)-4-[1-(4-cyanobenzyl)-5-imidazolylmethyl]-2-piperazinone, described in WO-00/01691 (Merck); compound 2(S)-[2(S)-[2(R)-amino-3-mercapto]propylamino-3(S)-methyl]-pentyloxy-3-phenylpropionyl-methionine sulfone described in WO-94/10138 (Merck); and BMS 214662, i.e. (R)-2,3,4,5-tetrahydro-1-(1H-imidazol-4-ylmethyl)-3-(phenylmethyl)-4-(2-thienylsulphonyl)-1H-1,4-benzodiazapine-7-carbonitrile, described in WO 97/30992 (Bristol Myers Squibb) and Pfizer compounds (A) and (B) described in WO-00/12498 and WO-00/12499:

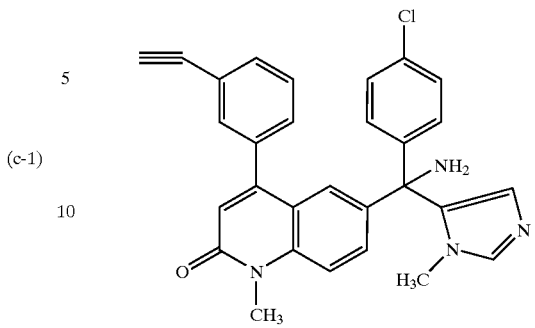 (A)

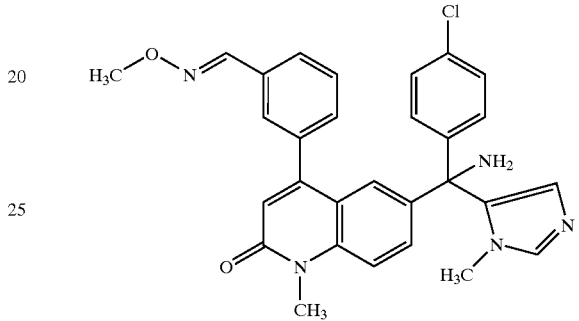 (B)

The compounds are generally described as being inhibitors of farnesyl protein transferase useful in the treatment of mammalian tumors. Generally in the treatment of cancerous tumors about 0.01 mg/kg to 100 mg/kg body weight of a farnesyl protein transferase inhibitor is administered at doses of about two, three, four or more sub doses at appropriate intervals throughout the day. This dosing schedule is predicated on the hypothesis that continuous exposure to the active compound and resultant inhibition of FPT were required in order to maintain antitumor effects.

Unexpectedly, it has been found that an interrupted dosing regimen of about five days containing a farnesyl protein transferase inhibitor as the active ingredient followed by about two weeks without treatment results in suppression of mammalian tumor growth.

It is an object of the present invention to provide a method of treatment and a dosing regimen comprising a discontinuous dosing schedule in which a farnesyl protein transferase inhibitor is administered to suppress mammalian tumor growth. The regimen comprises the administration of a single dose of a farnesyl protein transferase inhibitor over a one to five day period followed by at least two weeks without treatment.

SUMMARY OF THE INVENTION

The present invention relates to a method of treating mammalian tumors which comprises administering a single dose of a farnesyl protein transferase inhibitor over a one to five day period. The invention also relates to an antitumor dosage regimen in which suppression of tumor growth is achieved by the administration of a farnesyl protein transferase inhibitor over a one to five day period followed by at least two weeks without treatment. The transient one to five day exposure of mammalian tumors to a farnesyl protein transferase inhibitor produces sustained antitumor effects. The inhibition of FPT by a FPT inhibitor under the method and regimen of the present invention produces lasting alterations in the malignant process which recover only very slowly.

DETAILED DESCRIPTION OF THE INVENTION

Inhibitors of farnesyl transferase (FPT) are known to be useful in the treatment of mammalian tumors and in particular colon and pancreatic carcinomas. In previous studies farnesyl protein transferase inhibitors have been shown to inhibit the growth of mammalian tumors when administered as a twice daily dosing schedule. It has been unexpectedly been found that administration of a farnesyl protein transferase inhibitor in a single dose daily for one to five days produced a marked suppression of tumor growth lasting out to at least 21 days. In particular, administration of a farnesyl protein transferase inhibitor at a single dose between 50–1200 mg/kg body weight once daily for one to five consecutive days after tumor formation produces a marked suppression of tumor growth lasting out to 21 or more days. The effect is equivalent to administering a farnesyl protein transferase inhibitor continuously at a daily 50 mg/kg-100 mg/kg dose in the same tumor model. Upon the appearance of growth in tumors treated according to the method and/or regimen of this invention, rechallenge with the FPT inhibitor at day 21 produced growth arrest indicating that tumor growth did not emerge from resistant tumor cells. Suppression of tumor growth was dose-related at doses from 50–1200 mg/kg body weight with the five day single dosing schedule. The preferred dosage range is 50–400 mg/kg with 200 mg/kg being the most preferred dose. In man based on early Phase 1 data, the preferred dose range of 200 to 2400 mg can be expected. The finding that a persistent suppression of tumor growth can be obtained with only one to five days of treatment with a farnesyl protein transferase inhibitor was unexpected since it has been assumed that farnesyl protein transferase inhibitors as a class would require chronic continuous exposure in order to maintain uninterrupted inhibition of protein farnesylation.

Examples of FTI inhibitors which may be employed in accordance with the present invention include compounds of formula (I), (II), (III), (IV), (V), (VI), (VII), (VIII) or (IX) above, more particularly compounds of formula (I), (II) or (III):

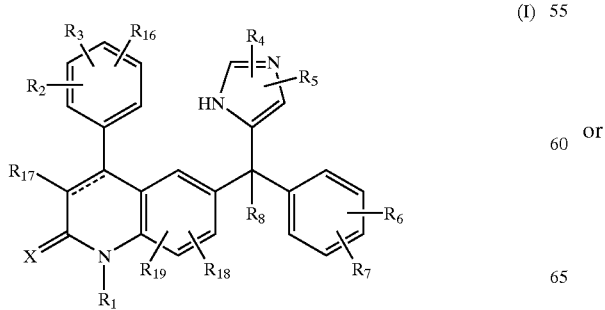
(I)

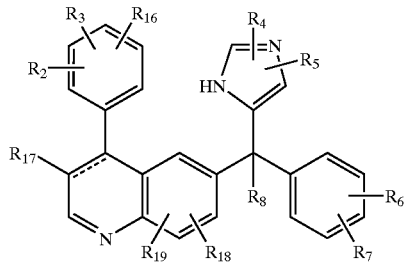
(II)

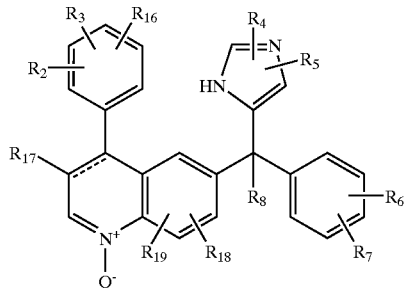
(III)

the pharmaceutically acceptable acid or base addition salts and the stereochemically isomeric forms thereof, wherein the dotted line represents an optional bond;

X is oxygen or sulfur;

$R^1$ is hydrogen, $C_{1-12}$alkyl, $Ar^1$, $Ar^2C_{1-6}$alkyl, quinolinylC$_{1-6}$alkyl, pyridyl-$C_{1-6}$alkyl, hydroxyC$_{1-6}$alkyl, $C_{1-6}$alkyloxyC$_{1-6}$alkyl, mono- or di($C_{1-6}$alkyl)-aminoC$_{1-6}$alkyl, aminoC$_{1-6}$alkyl, or a radical of formula —Alk$^1$—C(=O)—R$^9$, —Alk$^1$—S(O)—R$^9$ or —Alk$^1$—S(O)$_2$—R$^9$, wherein Alk$^1$ is $C_{1-6}$alkanediyl, $R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;

$R^2$, $R^3$ and $R^{16}$ each independently are hydrogen, hydroxy, halo, cyano, $C_{1-6}$alky, $C_{1-6}$alkyloxy, hydroxyC$_{1-6}$alkyloxy, $C_{1-6}$alkyloxyC$_{1-6}$alkyloxy, aminoC$_{1-6}$alkyloxy, mono- or di($C_{1-6}$alkyl)aminoC$_{1-6}$alkyloxy, Ar$^1$, Ar$^2$C$_{1-6}$alkyl, Ar$^2$oxy, Ar$^2$C$_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or when on adjacent positions $R^2$ and $R^3$ taken together may form a bivalent radical of formula —O—CH$_2$—O— (a-1)

—O—CH$_2$—CH$_2$—O— (a-2)

—O—CH=CH— (a-3)

—O—CH$_2$—CH$_2$— (a-4)

—O—CH$_2$—CH$_2$—CH$_2$— (a-5)

or

—CH=CH—CH=CH— (a-6)

$R^4$ and $R^5$ each independently are hydrogen, halo, Ar$^1$, $C_{1-6}$alkyl, hydroxyC$_{1-6}$alkyl, $C_{1-6}$alkyloxyC$_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2$$C_{1-6}$alkyl;

$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di($C_{1-6}$alkyl)amino, or when on adjacent positions $R^6$ and $R^7$ taken together may form a bivalent radical of formula —O—CH$_2$—O— (c-1)

or

—CH=CH—CH=CH— (c-2)

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di($C_{1-6}$alkyl)amino$C_{1-6}$alkyl, imidazolyl, halo$C_{1-6}$alkyl, $C_{1-6}$alkyloxy$C_{1-6}$alkyl, aminocarbonyl$C_{1-6}$alkyl, or a radical of formula —O—$R^{10}$ (b-1)

—S—$R^{10}$ (b-2)

—N—$R^{11}R^{12}$ (b-3)

wherein $R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonyl$C_{1-6}$alkyl, or a radical or formula —Alk$^2$—OR$^{13}$ or —Alk$^2$—NR$^{14}R^{15}$;
$R^{11}$ is hydrogen, $C_{1-12}$alkyl, $Ar^1$ or $Ar^2C_{1-6}$alkyl;
$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, $Ar^1$, $Ar^2C_{1-6}$alkyl, $C_{1-6}$alkylcarbonyl-$C_{1-6}$alkyl, a natural amino acid, $Ar^1$carbonyl, $Ar^2C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonylamino, $C_{1-6}$alkylamino, $C_{1-6}$alkylcarbonylamino, or a radical or formula —Alk$^2$—OR$^{13}$ or —Alk$^2$—NR$^{14}R^{15}$;
wherein Alk$^2$ is $C_{1-6}$alkanediyl;
$R^{13}$ is hydrogen, $C_{1-6}$alkyl, $C_{1-6}$alkylcarbonyl, hydroxy-$C_{1-6}$alkyl, $Ar^1$ or $Ar^2C_{1-6}$alkyl;
$R^{14}$ is hydrogen, $C_{1-6}$alkyl, $Ar^1$ or $Ar^2C_{1-6}$alkyl;
$R^{15}$ is hydrogen, $C_{1-6}$alkyl, $C_{1-6}$alkylcarbonyl, $Ar^1$ or $Ar^2C_{1-6}$alkyl;

$R^{17}$ is hydrogen, halo, cyano, $C_{1-6}$alkyl, $C_{1-6}$alkyloxycarbonyl, $Ar^1$;
$R^{18}$ is hydrogen, $C_{1-6}$alkyl, $C_{1-6}$alkyloxy or halo;
$R^{19}$ is hydrogen or $C_{1-6}$alkyl;
$Ar^1$ is phenyl or phenyl substituted with $C_{1-6}$alkyl, hydroxy, amino, $C_{1-6}$alkyloxy or halo; and
$Ar^2$ is phenyl or phenyl substituted with $C_{1-6}$alkyl, hydroxy, amino, $C_{1-6}$alkyloxy or halo.

In Formulas (I), (II) and (III), $R^4$ or $R^5$ may also be bound to one of the nitrogen atoms in the imidazole ring. In that case the hydrogen on the nitrogen is replaced by $R^4$ or $R^5$ and the meaning of $R^4$ and $R^5$ when bound to the nitrogen is limited to hydrogen, $Ar^1$, $C_{1-6}$alkyl, hydroxy$C_{1-6}$alkyl, $C_{1-6}$alkyloxy$C_{1-6}$alkyl, $C_{1-6}$alkyloxycarbonyl, $C_{1-6}$alkylS(O)$C_{1-6}$alkyl, $C_{1-6}$alkylS(O)$_2C_{1-6}$alkyl.

Preferably the substituent $R^{18}$ is situated on the 5 or 7 position of the quinolinone moiety and substituent $R^{19}$ is situated on the 8 position when $R^{18}$ is on the 7-position.

Interesting compounds are these compounds of formula (I) wherein X is oxygen.

Also interesting compounds are these compounds of formula (I) wherein the dotted line represents a bond, so as to form a double bond.

Another group of interesting compounds are those compounds of formula (I) wherein $R^1$ is hydrogen, $C_{1-6}$alkyl, $C_{1-6}$alkyloxy$C_{1-6}$alkyl, di($C_{1-6}$alkyl)amino$C_{1-6}$alkyl, or a radical of formula —Alk$^1$—C(=O)—$R^9$, wherein Alk$^1$ is methylene and $R^9$ is $C_{1-8}$alkyl-amino substituted with $C_{1-6}$alkyloxycarbonyl.

Still another group of interesting compounds are those compounds of formula (I) wherein $R^3$ is hydrogen or halo; and $R^2$ is halo, $C_{1-6}$alkyl, $C_{2-6}$alkenyl, $C_{1-6}$alkyloxy, trihalomethoxy or hydroxy$C_{1-6}$alkyloxy.

A further group of interesting compounds are those compounds of formula (I) wherein $R^2$ and $R^3$ are on adjacent positions and taken together to form a bivalent radical of formula (a-1), (a-2) or (a-3).

A still further group of interesting compounds are those compounds of formula (I) wherein $R^5$ is hydrogen and $R^4$ is hydrogen or $C_{1-6}$alkyl.

Yet another group of interesting compounds are those compounds of formula (I) wherein $R^7$ is hydrogen; and $R^6$ is $C_{1-6}$alkyl or halo, preferably chloro, especially 4-chloro.

A particular group of compounds are those compounds of formula (I) wherein $R^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula NR$^{11}R^{12}$ wherein $R^{11}$ is hydrogen or $C_{1-12}$alkyl and $R^{12}$ is hydrogen, $C_{1-6}$alkyl, $C_{1-6}$alkyloxy, hydroxy, $C_{1-6}$alkyloxy$C_{1-6}$alkylcarbonyl, or a radical of formula —Alk$^2$—OR$^{13}$ wherein $R^{13}$ is hydrogen or $C_{1-6}$alkyl.

Preferred compounds are those compounds wherein $R^1$ is hydrogen, $C_{1-6}$alkyl, $C_{1-6}$alkyloxy$C_{1-6}$alkyl, di($C_{1-6}$alkyl)amino$C_{1-6}$alkyl, or a radical of formula —Alk$^1$—C(=O)—$R^9$, wherein Alk$^1$ is methylene and $R^9$ is $C_{1-8}$alkylamino substituted with $C_{1-6}$alkyloxycarbonyl; $R^2$ is halo, $C_{1-6}$alkyl, $C_{2-6}$alkenyl, $C_{1-6}$alkyloxy, trihalomethoxy, hydroxy$C_{1-6}$alkyloxy or $Ar^1$; $R^3$ is hydrogen; $R^4$ is methyl bound to the nitrogen in 3-position of the imidazole; $R^5$ is hydrogen; $R^6$ is chloro; $R^7$ is hydrogen; $R^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula —NR$^{11}R^{12}$ wherein $R^{11}$ is hydrogen or $C_{1-12}$alkyl and $R^{12}$ is hydrogen, $C_{1-6}$alkyl, $C_{1-6}$alkyloxy, $C_{1-6}$alkyloxy$C_{1-6}$alkylcarbonyl, or a radical of formula —Alk$^2$—OR$^{13}$ wherein $R^{13}$ is $C_{1-6}$alkyl; $R^{17}$ is hydrogen and $R^{18}$ is hydrogen.

Most preferred compounds are
4-(3-chlorophenyl)-6-[(4-chlorophenyl)hydroxy(1-methyl-1H-imidazol-5-yl)methyl]-1-methyl-2(1H)-quinolinone, 6-[amino(4-chlorophenyl)-1-methyl-1H-imidazol-5-ylmethyl]-4-(3-chlorophenyl)-1-methyl-2 (1H)-quinolinone;

6-[(4-chlorophenyl)hydroxy(1-methyl-1H-imidazol-5-yl) methyl]-4-(3-ethoxyphenyl)-1-methyl-2(1H)-quinolinone;

6-[(4-chlorophenyl)(1-methyl-1H-imidazol-5-yl)methyl]-4-(3-ethoxyphenyl)-1-methyl-2(1H)-quinolinone monohydrochloride.monohydrate;

6-[amino(4-chlorophenyl)(1-methyl-1H-imidazol-5-yl) methyl]-4-(3-ethoxyphenyl)-1-methyl-2(1H)-quinolinone, 6-amino(4-chlorophenyl)(1-methyl-1H-imidazol-5-yl)methyl]-1-methyl-4-(3-propylphenyl)-2 (1H)-quinolinone; a stereoisomeric form thereof or a pharmaceutically acceptable acid or base addition salt; and (+)-6-[amino(4-chlorophenyl)(1-methyl-1H-imidazol-5-yl)methyl]-4-(3-chlorophenyl)-1-methyl-2(1H)-quinolinone (Compound 75 in Table 1 of the Experimental part of WO-97/21701); or a pharmaceutically acceptable acid addition salt thereof. The latter compound is especially preferred.

Further preferred embodiments of the present invention include compounds of formula (IX) wherein one or more of the following restrictions apply:

=$X^1$—$X^2$—$X^3$ is a trivalent radical of formula (x-1), (x-2), (x-3), (x-4) or (x-9) wherein each $R^6$ independently is hydrogen, $C_{1-4}$alkyl, $C_{1-4}$alkyloxycarbonyl, amino or aryl and $R^7$ is hydrogen;

>y1-y2- is a trivalent radical of formula (y-1), (y-2), (y-3), or (y-4) wherein each $R^9$ independently is hydrogen, halo, carboxyl, $C_{1-4}$alkyl or $C_{1-4}$alkyloxycarbonyl;

r is 0, 1 or 2;

s is 0 or 1;

t is 0;

$R^1$ is halo, $C_{1-6}$alkyl or two $R^1$ substituents ortho to one another on the phenyl ring may independently form together a bivalent radical of formula (a-1);

$R^2$ is halo;

$R^3$ is halo or a radical of formula (b-1) or (b-3) wherein $R^{10}$ is hydrogen or a radical of formula —Alk—$OR^{13}$.

$R^{11}$ is hydrogen;

$R^{12}$ is hydrogen, $C_{1-6}$alkyl, $C_{1-6}$alkylcarbonyl, hydroxy, $C_{1-6}$alkyloxy or mono- or di($C_{1-6}$alkyl)amino$C_{1-6}$alkylcarbonyl;

Alk is $C_{1-6}$alkanediyl and $R^{13}$ is hydrogen;

$R^4$ is a radical of formula (c-1) or (c-2) wherein $R^{16}$ is hydrogen, halo or mono- or di($C_{1-4}$alkyl)amino;

$R^{17}$ is hydrogen or $C_{1-6}$alkyl;

aryl is phenyl.

A particular group of compounds consists of those compounds of formula (IX) wherein =2 $X^1$-$X^2$-$X^3$ is a trivalent radical of formula (x-1), (x-2), (x-3), (x-4) or (x-9), >Y1-Y2 is a trivalent radical of formula (y-2), (y-3) or (y-4), r is 0 or 1, s is 1, t is 0, $R^1$ is halo, $C_{1-4}$)alkyl or forms a bivalent radical of formula (a-1), $R^2$ is halo or $C_{1-4}$alkyl, $R^3$ is hydrogen or a radical of formula (b-1) or (b-3), $R^4$ is a radical of formula (c-1) or (c-2), $R^6$ is hydrogen, $C_{1-4}$alkyl or phenyl, $R^7$ is hydrogen, $R^9$ is hydrogen or $C_{1-4}$alkyl, $R^{10}$ is hydrogen or —Alk—$OR^{13}$, $R^{11}$ is hydrogen and $R^{12}$ is hydrogen or $C_{1-6}$alkylcarbonyl and $R^{13}$ is hydrogen;

Preferred compounds are those compounds of formula (IX) wherein =$X^1$-$X^2$-$X^3$ is a trivalent radical of formula (x-1) or (x-4), >Y1-Y2 is a trivalent radical of formula (y-4), r is 0 or 1, s is 1, t is 0, $R^1$ is halo, preferably chloro and most preferably 3-chloro, $R^2$ is halo, preferably 4-chloro or 4-fluoro, $R^3$ is hydrogen or a radical of formula (b-1) or (b-3), $R^4$ is a radical of formula (c-1) or (c-2), $R^6$ is hydrogen, $R^7$ is hydrogen, $R^9$ is hydrogen, $R^{10}$ is hydrogen, $R^{11}$ is hydrogen and $R^{12}$ is hydrogen;

Other preferred compounds are those compounds of formula (IX) wherein -$X^1$-$X^2$-$X^3$ is a trivalent radical of formula (x-2), (x-3) or (x-4), >Y1-Y2 is a trivalent radical of formula (y-2), (y-3) or (y-4), r and s are 1, t is 0, $R^1$ is halo, preferably chloro, and most preferably 3-chloro or $R^1$ is $C_{1-4}$alkyl, preferably 3-methyl, $R^2$ is halo, preferably chloro, and most preferably 4-chloro, $R^3$ is a radical of formula (b-1) or (b-3), $R^4$ is a radical of formula (c-2), $R^6$ is $C_{1-4}$alkyl, $R^9$ is hydrogen, $R^{10}$ and $R^{11}$ are hydrogen and $R^{12}$ is hydrogen or hydroxy.

The most preferred compounds of formula (IX) are
7-[(4-fluorophenyl)(1H-imidazol-1-yl)methyl]-5-phenylimidazo[1,2-a]quinoline; α-(4-chlorophenyl)-α-(1-methyl-1H-imidazol-5-yl)-5-phenylimidazo,[1,2-a] quinoline-7-methanol;

5-(3-chlorophenyl)-α-(4-chlorophenyl)-α-( 1-methyl-1H-imidazol-5-yl)-imidazo[1,2-a-]quinoline-7-methanol;

5-(3-chlorophenyl)-α-(4-chlorophenyl)-α-(1-methyl-1H-imidazol-5-yl)imidazo[1,2-a-]quinoline-7-methanamine;

5-(3-chlorophenyl)-α-(4-chlorophenyl)-α-(1-methyl-1H-imidazol-5-yl)tetrazolo[1,5-a]quinoline-7-methanamine;

5-(3-chlorophenyl)-α-(4-chlorophenyl)-1-methyl-α-1-methyl-1H-imidazol-5-yl)-1,2,4-triazolo[4,3-a] quinoline-7-methanol;

5-(3-chlorophenyl)-α-(4-chlorophenyl)-α-(1-methyl-1H-imidazol-5-yl)tetrazolo[1,5-a]quinoline-7-methanamine;

5-(3-chlorophenyl)-α-(4-chlorophenyl)-α-(1-methyl-1H-imidazol-5-yl)tetrazolo[1,5-a]quinazoline-7-methanol;

5-(3-chlorophenyl)-α-(4-chlorophenyl)-4,5-dihydro-α-(1-methyl-1H-imidazol-5-yl)tetrazolo[1,5-a] quinazoline-7-methanol;

5-(3-chlorophenyl)-α-(4-chlorophenyl)-α-(1-methyl-1H-imidazol-5-yl)tetrazolo[1,5-a]quinazoline-7-methanamine;

5-(3-chlorophenyl)-α-(4-chlorophenyl)-N-hydroxy-α-(1-methyl-1H-imidazol-5-yl)tetrahydro[1,5-a]quinoline-7-methanamine;

α-(4-chlorophenyl)-α-(1-methyl-1H-imidazol-5-yl)-5-(3-methylphenyl)tetrazolo [1,5-a]quinoline-7-methanamine; the pharmaceutically acceptable acid addition salts and the stereochemically isomeric forms thereof.

5-(3-chlorophenyl)-α-(4-chlorophenyl)-α-(1-methyl-1H-imidazol-5-yl)tetrazolo[1,5-a]quinazoline-7-methanamine, especially the (-) enantiomer, and its pharmaceutically acceptable acid addition salts are especially preferred.

As used in the foregoing definitions and hereinafter halo defines fluoro, chloro, bromo and iodo; $C_{1-6}$alkyl defines straight and branched chained saturated hydrocarbon radicals having from 1 to 6 carbon atoms such as, for example, methyl, ethyl, propyl, butyl, pentyl, hexyl and the like; $C_{1-8}$alkyl encompasses the straight and branched chained saturated hydrocarbon radicals as defined in $C_{1-6}$alkyl as well as the higher homologues thereof containing 7 or 8 carbon atoms such as, for example heptyl or octyl; $C_{1-12}$alkyl again encompasses $C_{1-8}$alkyl and the higher homologues thereof containing 9 to 12 carbon atoms, such as, for example, nonyl, decyl, undecyl, dodecyl; $C_{1-16}$alkyl again encompasses $C_{1-12}$alkyl and the higher homologues thereof containing 13 to 16 carbon atoms, such as, for example, tridecyl, tetradecyl, pentedecyl and hexadecyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof. The term "C(=O)" refers to a carbonyl group, "S(O)" refers to a sulfoxide and "S(O)$_2$" to a sulfon. The term "natural amino acid" refers to a natural amino acid that is bound via a covalent amide linkage formed by loss of a molecule of water between the carboxyl group of the amino acid and the amino group of the remainder of the molecule. Examples of natural amino acids are glycine, alanine, valine, leucine, isoleucine, methionine, proline, phenylanaline, tryptophan, serine, threonine, cysteine, tyrosine, asparagine, glutamine, aspartic acid, glutamic acid, lysine, arginine, histidine.

The pharmaceutically acceptable acid or base addition salts as mentioned hereinabove are meant to comprise the therapeutically active non-toxic acid and non-toxic base addition salt forms which the compounds of formulas (I), (II), (III), (IV), (V), (VI), (VII), (VIII) or (IX) are able to form. The compounds of formulas (I), (II), (III), (IV), (V), (VI), (VII), (VIII) or (IX) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formulae (I), (II), (III), (IV), (V), (VI), (VII), (VIII) or (IX) which have acidic properties may be converted in their pharmaceutically acceptable base addition salts by treating said acid form with a suitable organic or inorganic base.

Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formulae (I), (II), (III), (IV), (V), (VI), (VII), (VIII) or (IX) are able to form. Examples of such forms are e.g. hydrates, alcoholates and the like.

The term stereochemically isomeric forms of compounds of formulae (I), (II), (III), (IV), (V), (VI), (VII), (VIII) or (IX), as used hereinbefore, defines all possible compounds made up of the same atoms bonded by the same sequence of bonds but having different three-dimensional structures which are not interchangeable, which the compounds of formulae (I), (II), (III), (IV), (V), (VI), (VII), (VIII) or (IX) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formulae (I), (II), (III), (IV), (V), (VI), (VIII), (VIII) or (IX) both in pure form or in admixture with each other are intended to be embraced within the scope of the present invention.

Some of the compounds of formulae (I), (II), (III), (IV), (V), (VI), (VII), (VIII) or (IX) may also exist in their tautomeric forms. Such forms although not explicitly indicated in the above formula are intended to be included within the scope of the present invention.

Whenever used hereinafter, the term "compounds of formulae(I), (II), (III), (IV), (V), (VI), (VII), (VIII) or (IX)" is meant to include also the pharmaceutically acceptable acid or base addition salts and all stereoisomeric forms.

Other farnesyl protein transferase inhibitors which can be employed in accordance with the present include Arglabin, perrilyl alcohol, SCH-66336, 2(S)-[2(S)-[2(R)-amino-3-mercapto]propylamino-3(S)-methyl]-pentyloxy-3-phenylpropionyl-methionine sulfone (Merck); L778123, BMS 214662, Pfizer compounds A and B described above. These compounds can be prepared, for example, by methods described in the relevant patent specifications identified above which are incorporated herein by reference.

Suitable dosages for the compounds Arglabin (WO98/28303), perrilyl alcohol (WO 99/45712), SCH-66336 (U.S. Pat. No. 5,874,442), L778123 (WO 00/01691), 2(S)-[2(S)-[2(R)-amino-3-mercapto]propylamino-3(S)-methyl]-pentyloxy-3-phenylpropionyl-methionine sulfone (WO94/10138), BMS 214662 (WO 97/30992), Pfizer compounds A and B (WO 00/12499 and WO 00/12498) are given in the aforementioned patent specifications which are incorporated herein by reference or are known to or can be readily determined by a person skilled in the art.

In relation to perrilyl alcohol, the medicament may be administered 1-4g per day per 150 lb human patient. Preferably, 1–2 g per day per 150 lb human patient. SCH-66336 typically may be administered in a unit dose of about 0.1 mg to 100 mg, more preferably from about 1 mg to 300 mg according to the particular application. Compounds L778123 and 1-(3-chlorophenyl)-4-[1-(4-cyanobenzyl)-5-imidazolylmethyl]-2-piperazinone may be administered to a human patient in an amount between about 0.1 mg/kg of body weight to about 20 mg/kg of body weight per day, preferably between 0.5 mg/kg of bodyweight to about 10 mg/kg of body weight per day.

Pfizer compounds A and B may be administered in dosages ranging from about 1.0 mg up to about 500 mg per day, preferably from about 1 to about 100 mg per day in single or divided (i.e. multiple) doses. Therapeutic compounds will ordinarly be administered in daily dosages ranging from about 0.01 to about 10 mg per kg body weight per day, in single or divided doses.

BMS 214662 may be administered in a dosage range of about 0.05 to 200 mg/kg/day, preferably less than 100 mg/kg/day in a single dose or in 2 to 4 divided doses.

This invention is especially applicable to the treatment of tumors expressing an activated ras oncogene. Examples of tumors which may be inhibited include, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carninoma, ovary carcinoma, bladder carcinoma and epidermal carcinoma.

Farnesyl protein transferase inhibitors can be prepared and formulated into pharmaceutical compositions by methods known in the art and in particular according to the methods described in the published patent specifications, United States Patents, and United States Patent Applications, mentioned herein and incorporated by reference; for the compounds of formulae (I), (II) and (III) suitable examples can be found in WO-97/21701, and it's United States counterpart, U.S. Pat. No. 6,037,350. Compounds of formulae (IV), (V), and (VI) can be prepared and formulated using methods described in WO 97/16443, and it's United States counterpart, U.S. Pat. No. 5,968,952; compounds of formulae (VII) and (VIII) according to methods described in WO 98/40383 and WO 98/49157, and their United States counterparts, U.S. Pat. Nos. 6,187,786 and 6,177,432, respectively; and compounds of formula (IX) according to methods described in WO 00/39082, and it's United States counterpart, U.S. patent application Ser. No. 09/868,992. To prepare the aforementioned pharmaceutical compositions, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The above farnesyl trasferase inhibitor may be used in combination with one or more other anti-cancer agents such as platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carmustine or lomustine, anti-tumor anthracycline derivatives for example daunorubicin, doxorubicin, idarubicin or epirubicin; HER2 antibodies for example trastzumab; anti-tumor podophyllotoxin derivatives for example etoposide or teniposide; and antiestrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

The farnesyl transferase inhibitor and the further anti-cancer agent may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular farnesyl transferase inhibitor and further anti-cancer agents being administered, their route of administration, the particular tumor being treated and the particular host being treated. The optimum method and order of administration and the dosage amounts and regime can be readily determined by those skilled in the art using conventional methods and in view of the information set out herein.

The FPT inhibitor for use in accordance with the present invention may be prepared in a conventional manner, for example, by the processes described in the above patent specifications The following examples describe the invention in greater detail and are intended to illustrate but not to limit the invention.

EXAMPLE 1

Materials and Methods

Cell Culture: CAPAN-2 human pancreatic carcinoma cells were purchased from the American Type Culture Collection (Rockville, Md.). Cells were maintained in McCoys 5A Medium supplemented with 10% fetal calf serum and penicillin-streptomycin. NIH 3T3 cells transfected with the activated T24 H-ras oncogene (T24 cells ) were obtained from, Janssen Research Foundation (For methods see Parada, L. F., Tabin, C. J., Shih, C., and Weinberg, R Human EJ bladder carcinoma oncogene is homologue of Harvey sarcoma virus ras gene. Nature 297: 474–478, 1982.; Santos, E., Tronick, S. R., Aaronson, S. A., Pulciani, S., and Barbacid, M. T24 human bladder carcinoma oncogene is an activated form of the normal human homologue of BALB-and Harvey-MSV transforming genes. Nature 298: 343–347, 1982.) T24 cells were maintained as monolayer cultures in Dulbecco's Modified Eagle's Medium (DMEM) supplemented with 10% Nu-serum Type IV (Collaborative Biomedical Products, Bedford, Mass. and 40 µg/ml G418 (Geneticin®, GIBCO-BRL, Gaithersburg, Md.).

Animals: Female nu/nu immunodeficient nude mice (42 days old) were purchased from Charles River Laboratories (Wilmington, Mass.). Mice were housed five per cage in microisolator cages placed in laminar flow shelving to maintain sterility. All bedding, food, water and cages were autoclaved. Animals were handled within the sterile confines of a laminar flow cabinet. The mice were otherwise maintained under standard vivarium conditions. Tumor studies were conducted under a protocol approved by the Institutional Animal Care and Use Committee.

Tumor Studies In Nude Mice: Cells growing as monolayers in T150 tissue culture flasks were detached by trypsinization with 10 ml of 0.05% trypsin plus 0.53 mM EDTA per flask. Tumor cell suspensions were pooled and trypsin was inactivated by the addition of serum containing medium (10 ml per 40 ml of trypsin cell suspension). Cells were collected by centrifugation and resuspended in Hank's Balanced Salt Solution (HBSS) warmed to 37° C. A 1.0 ml portion of cell suspension was added to 20 ml of diluent and counted on a Coulter particle counter. The cell suspensions were recentrifuged and resuspended at a concentration of $1 \times 10^6$ cell per 0.10 ml of HBSS. Mice were inoculated with a single subcutaneous injection of 0.10 ml of tumor cell suspension in the inguinal region. Mice were housed five per cage with 15 mice assigned to each treatment group. Body weight and tumor size as determined by caliper measurements were measured weekly. The caliper measurements of length and width were multiplied to obtain tumor areas. At the end of study, mice were sacrificed by $CO_2$ asphyxiation.

Three days after tumor inoculation, the five day treatment with (R)-6-[amino(4-chlorophenyl)(1-methyl-1H-imidazol-5yl)methyl]-4-(3-chlorophenyl)-1-methyl-2(1H)-quinolinone (compound 1) was initiated. Compound 1 was administered once daily by oral gavage in a 20% beta-cyclodextrin vehicle as a volume of 0.10 ml of solution per 10 gm body weight. Control groups received the same dosage volume of the 20% beta-cyclodextrin vehicle.

Compounds. Compound 1 was prepared for oral administration by dissolving the compound first as a 2x concentrated stock in 40% hydroxypropyl beta cyclodextrin (lot no. 051-071/1) in 0.1 N HCl. Compound 1 was dissolved by stirring vigorously approximately 30 minutes followed by sonication for 10 min. The compound 1 solutions were brought to a final concentration by diluting 1:1 with 0.1 N HCl. The final drug solutions were sterile filtered immediately and transferred to sterile tubes. Solutions were stored refrigerated and protected form light during the course of the study and sterility was maintained by opening solutions under sterile laminar flow conditions.

Results and Discussion

Presented in FIG. 1 are the results of studying intermittent dosing of compound 1. Compound 1 was administered once daily for five days every three weeks to nude mice bearing the T24 H-ras tumors. Vehicle treated animals presented with aggressively growing tumors 14 days after inoculation. This group was sacrificed on day 17 since their tumors exceeded the ethical guideline of a tumor burden no greater than 10% animal. body weight. Mice treated with 200 mg/kg compound I for five days (days 3–8 after tumor inoculation) presented with small tumors on day 17. Left untreated, the tumors returned to the rapid control growth rates by day 24. Animals were sacrificed on day 28 again according to ethical guidelines. A separate group of 15 mice received an additional 5-day treatment with 200 mg/kg compound 1. Tumor growth was again arrested but not as dramatically as in the initial treatment.

An identical dosing schedule was investigated in CAPAN-2 human pancreatic tumors in nude mice. Administration of compound 1 for five days at a dose of 200 mg/kg significantly reduced the growth of CAPAN-2 tumors out to day 24 (FIG. 2). Thereafter, tumors receiving no further treatment returned to the growth rate observed for vehicle treated controls. Again, a separate group of 15 animals received an additional five-day treatment with compound 1 on days 21 to 25. Only, a transient growth arrest, which was significant on day 28 of study, was produced. Although the response of the CAPAN-2 tumors was not as dramatic as the T24 tumors, the present results are remarkable when compared to previous studies. In our original evaluation of CAPAN-2 tumors with compound 1 administered twice daily on a continuous schedule for 18 days, doses of 50 mg/kg (100 mg/kg total daily dose) and 100 mg/kg (200 mg/kg) daily dose produced significant reductions of tumor growth. The five-day dosing schedule was a marked reduction in drug exposure from this previous study. Yet, an antitumor effect was still maintained The dose dependency of the abbreviated five-day dosing schedule was explored in T24 tumors at compound 1 doses of 50, 100 and 200 mg/kg. The duration of response was dose-related with the 200 mg dose again producing sustained effects out to day 17 of study (FIG. 3). The tumor suppressive effects of the lower doses waned by day 14. Significant, dose-related reductions of tumor growth measured as final tumor area (FIG. 4) and final tumor weights (FIG. 5) were still observed on day 17 of study for all compound 1 treatment groups. The highest tested dose of 200 mg/kg was substantially more effective than the lower does with a 90% reduction of final tumor weights observed.

Finally, to address the minimum duration of FPT inhibitor exposure required to elicit an antitumor effect, animals were treated with a single administration of compound 1. As shown in FIG. 6, a single 200 mg/kg or 400 mg/kg dose of compound 1 given three days after tumor inoculation produced a sustained inhibition of tumor growth lasting out to 15 days.

The present studies demonstrate that abbreviated five-day exposures to compound 1 can produce antitumor effects which persist for an additional two weeks or greater beyond the treatment.

Figure 1:
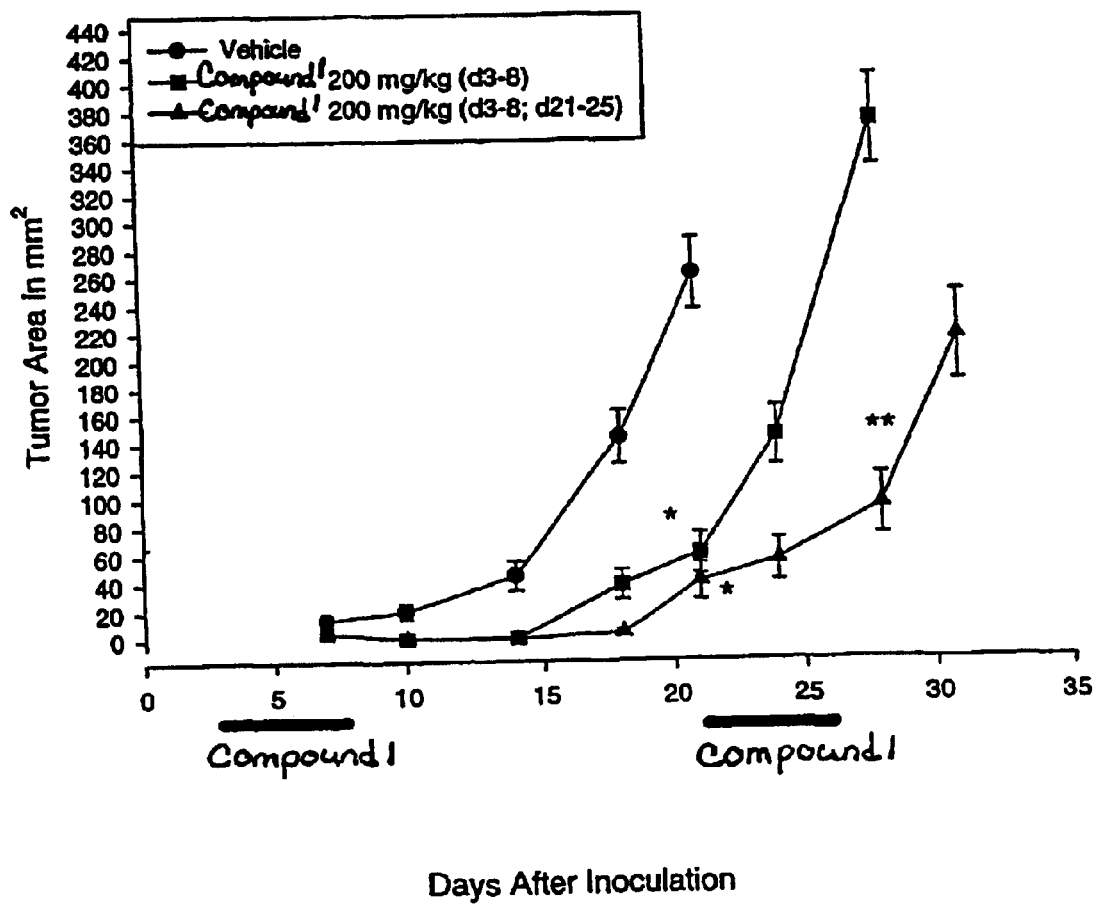
FIG. 1. Inhibition of the growth of T24 H-ras transformed NIH3T3 cell tumors by compound 1 administered as five-day intermittent treatments. Nude mice were inoculated with $1 \times 10^6$ T24 cells subcutaneously on day 0. After three days, oral dosing with beta-cyclodextrin vehicle (100 µl per 10 gm body weight) or compound 1 (200 mg/kg) was initiated. One treatment group was treated for an additional five days starting on day 21. Tumor size is expressed as tumor area (length×width). Values are means (±SEM) for N=14-15 animals per treatment group. For figure clarity, values significantly (p <0.05 by ANOVA) different from the vehicle treatment group are indicated (*) for day 21 only. Significant effects for the second treatment cycle with compound 1 are indicated for day 28 (**).
Figure 2:
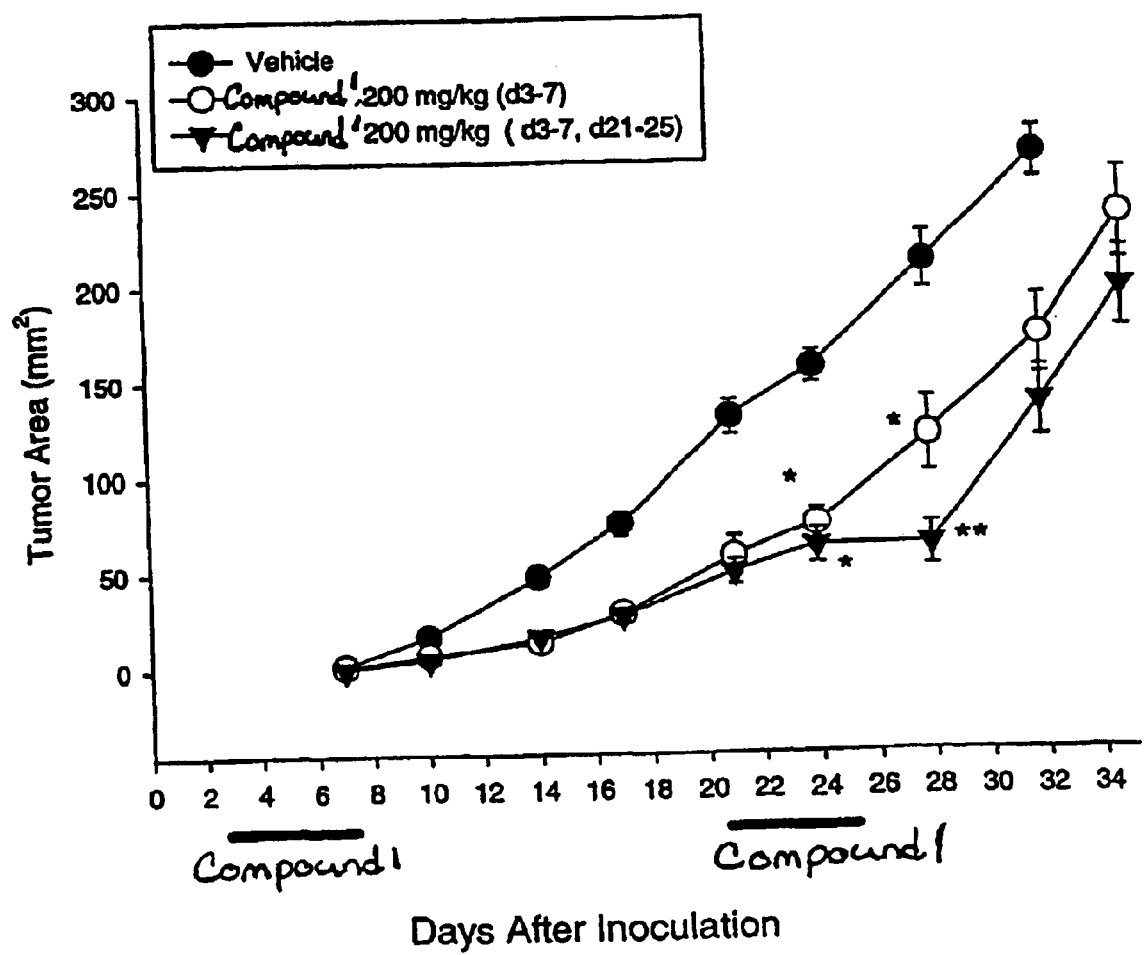
FIG. 2. Inhibition of tumor growth in CAPAN-2 human pancreatic tumors produced by intermittent five day treatments with compound 1 (200 mg/kg, p.o.) Nude mice were inoculated with $1 \times 10^6$ CAPAN-2 cells subcutaneously. After three days, oral dosing with beta-cyclodextrin vehicle (100 μl per 10 gm body weight) or compound 1 (200 mg/kg) was initiated. One treatment group was treated for an additional five days starting on day 21. Tumor size is expressed as tumor area (length×width). Values are means (±SEM) for N=14-15 animals per treatment group. For figure clarity, values significantly (p<0.05 by ANOVA) different from the vehicle treatment group are indicated (*) for day 24. Significant effects for the second treatment cycle with compound 1 are indicated for day 28 (**).
Figure 3:
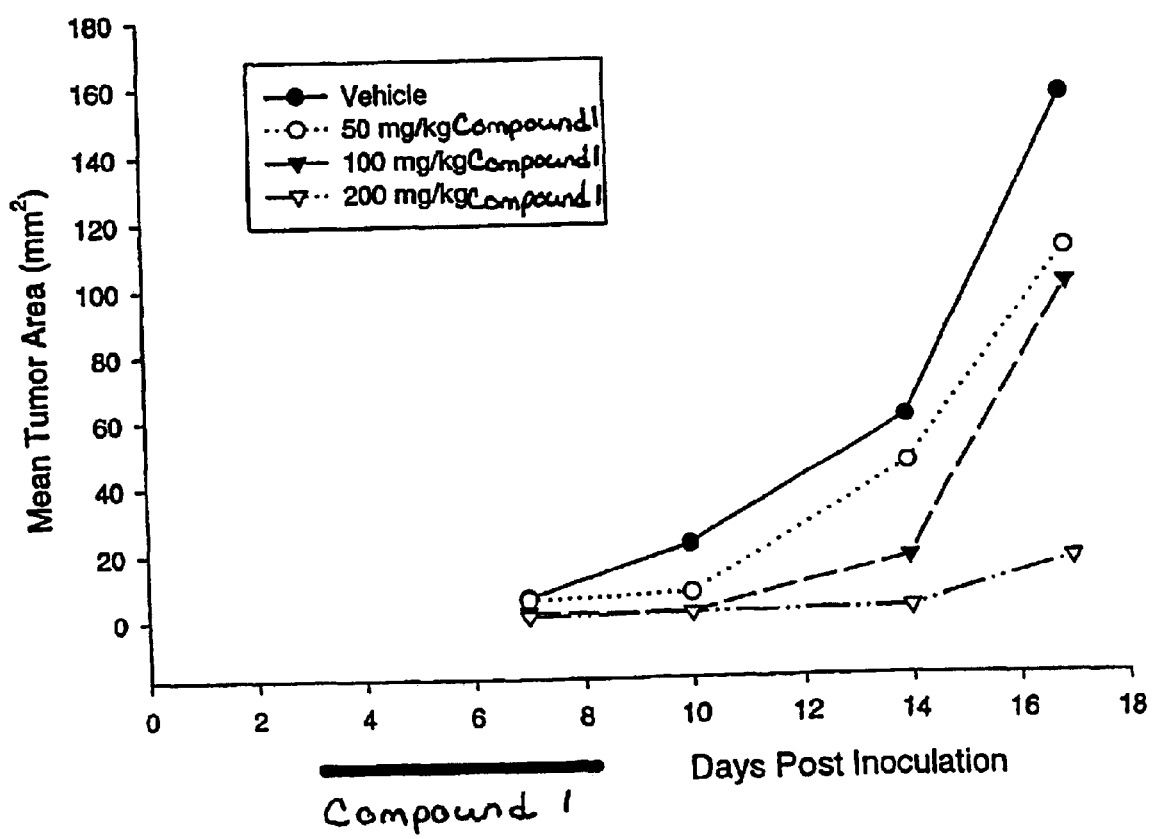
FIG. 3. Time course for inhibition of the growth of T24 U-ras transformed NIH3T3 cell tumors by compound 1 administered as a single five-day treatment. Nude mice were inoculated with $1 \times 10^6$ T24 cells subcutaneously on day 0. After three days, daily oral dosing with beta-cyclodextrin vehicle (100 μl per 10 gm body weight) or the indicated doses of compound 1 was initiated by oral gavage. Tumor size is expressed as tumor area (length×width). Values are means for N=14-15 animals per treatment group. Statistical analyses for tumor measurements collected at termination of study at day 17 are presented in FIGS. 4 and 5.
Figure 4:
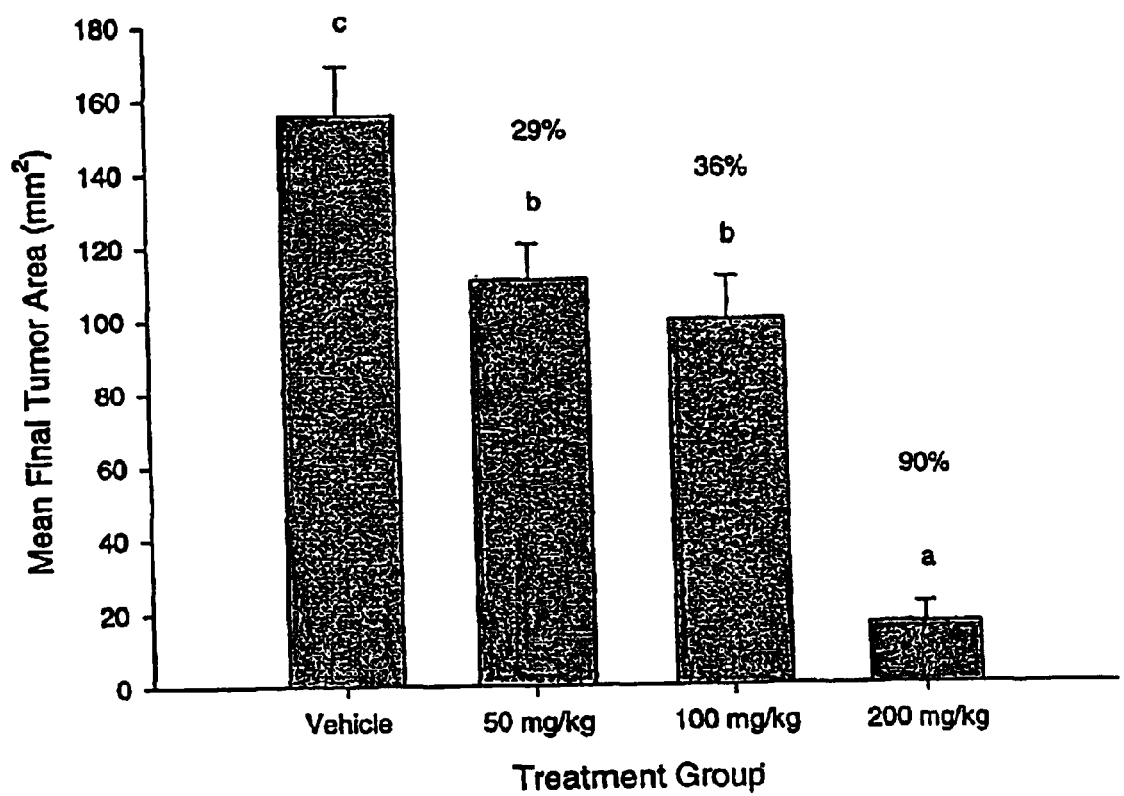
FIG. 4. Inhibition of the growth of T24 H-ras transformed NIH3T3 cell tumors by compound 1 administered as a single five-day treatment. Nude mice were inoculated with $1 \times 10^6$ T24 cells subcutaneously on day 0. After three days, oral dosing with beta-cyclodextrin vehicle (100 μl per 10 gm body weight) or the indicated doses of compound 1 was initiated by oral gavage. Tumor size is expressed as tumor area (length x width). Values are means (±SEM) for N=14-15 animals per treatment group. Values with the same letter are not significantly different (p<0.05 by ANOVA). The percent reduction in tumor size is presented over each histogram bar.
Figure 5:
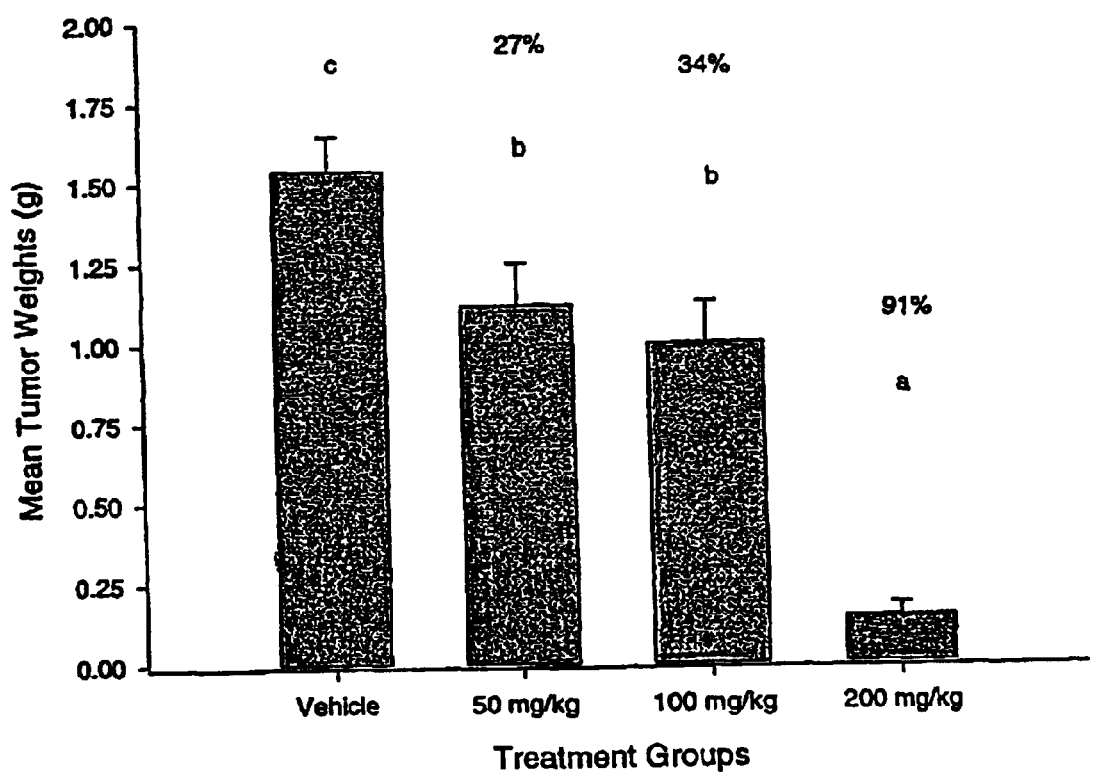
FIG. 5. Inhibition of the growth of T24 H-ras transformed NIH3T3 cell tumors by compound 1 administered as a single five-day treatment. Nude mice were inoculated with $1 \times 10^6$ T24 cells subcutaneously on day 0. After three days, oral dosing with beta-cyclodextrin vehicle (100 μl per 10 gm body weight) or the indicated doses of compound 1 was initiated by oral gavage. Tumor size is expressed as post mortem tumor weight (g). Values are means (±SEM) for N=14-15 animals per treatment group. Values with the same letter are not significantly different (p<0.05 by ANOVA). The percent reduction in tumor weight is indicated over each histogram bar.
Figure 6:
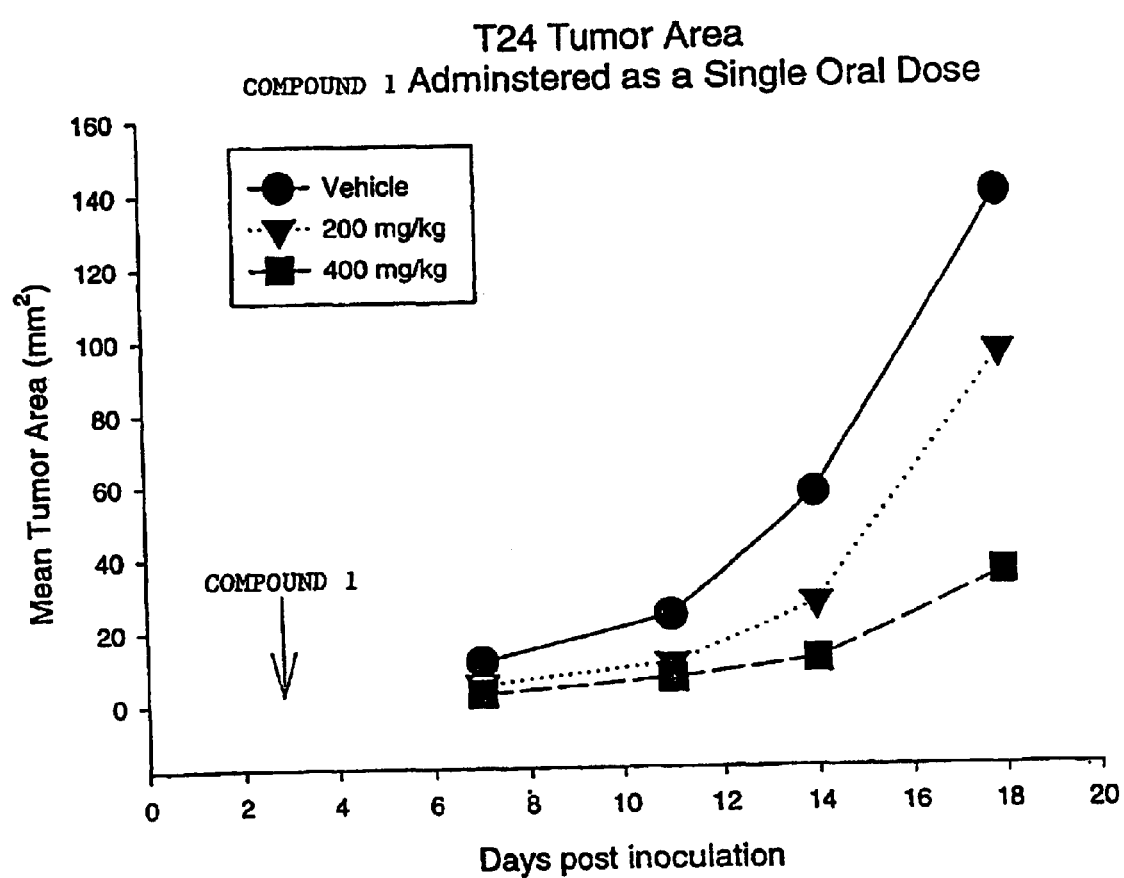
FIG. 6. Time course for inhibition of the growth of T24 H-ras transformed NIH3T3 cell tumors by compound 1 administered as a single-treatment. Nude mice were inoculated with $1 \times 10^6$ T24 cells subcutaneously on day 0. After three days, daily oral dosing with beta-cyclodextrin vehicle (100 μl per 10 gm body weight) or the indicated doses of compound 1 was initiated by oral gavage. Tumor size is expressed as tumor area (length x width). Values are means for N=14-15 animals per treatment group.

What is claimed is:

1. A method for the treatment of cancer in mammals which comprises administering a farnesyl protein transferase inhibitor once daily over a period of one to five days, followed by a period of at least fourteen days during which period no farnesyl transferase inhibitor is administered, the said farnesyl transferase inhibitor being a compound of formula (I):

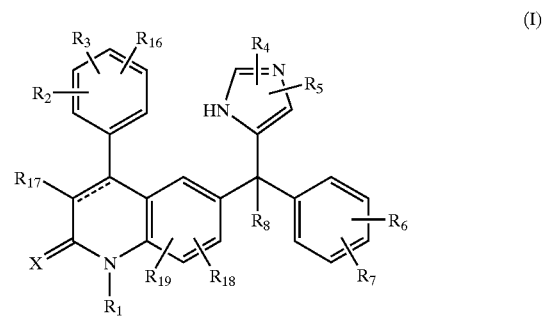

a stereoisomeric form thereof, a pharmaceutically acceptable acid or base addition salt thereof, wherein
the dotted line represents an optional bond;
X is oxygen or sulfur;
$R^1$ is hydrogen, $C_{1-12}$alkyl, $Ar^1$, $Ar^2C_{1-6}$alkyl, quinolinyl$C_{1-6}$alkyl, pyridyl-$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula —Alk$^1$—C(=O)—R$^9$, —Alk$^1$—S(O)—R$^9$ or —Alk$^1$—S(O)2—R$^9$, wherein Alk$^1$ is $C_{1-6}$alkanediyl,
$R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;
$R^2$, $R^3$ and $R^{16}$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, $Ar_1$, $AR^2C_{1-6}$alkyl, $AR^2$oxy, $AR^2C_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or
when on adjacent positions $R^2$ and $R^3$ taken together may form a bivalent radical of formula

 —O—CH$_2$—O— (a-1)

 —O—CH$_2$—CH$_2$—O— (a-2)

 —O—CH=CH— (a-3)

 —O—CH$_2$—CH$_2$— (a-4)

 —O—CH$_2$—CH$_2$—CH$_2$— (a-5)

or

 —CH=CH—CH=CH— (a-6)

$R^4$ and $R^5$ each independently are hydrogen, halo, $Ar^1$, $C_{1-6}$alkyl, hydroxy-$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2C_{1-6}$alkyl;
$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di($C_{1-6}$alkyl)amino, or
when on adjacent positions $R^6$ and $R^7$ taken together may form a bivalent radical of formula

 —O—CH$_2$—O— (c-1)

or

 —CH=CH—CH=CH— (c-2)

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di($C_{1-6}$alkyl)amino$C_{1-6}$alkyl, imidazolyl, halo$C_{1-6}$alkyl, $C_{1-6}$alkyloxy$C_{1-6}$alkyl, aminocarbonyl$C_{1-6}$alkyl, or a radical of formula —O—$R^{10}$ (b-1), —S—$R^{1-}$ )b-2), —N—$R^{11}R^{12}$ (b-3), wherein $R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonyl$C_{1-6}$alkyl, a radical or formula —$Alk^2$—$OR^{13}$ or —$Alk^2$—$NR^{14}R^{15}$;

$R^{11}$ is hydrogen, $C_{1-12}$alkyl, $Ar^1$ or $Ar^2C_{1-6}$alkyl;

$R^{12}$ is hydrogen, $C_{1-6}$alkyl, $C_{1-16}$alkylcarbonyl, $C_{1-6}$alkyloxycarbonyl, $C_{1-6}$alkylaminocarbonyl, $Ar^1$, $Ar^2C_{1-6}$alkyl, $C_{1-6}$alkylcarbonyl$C_{1-6}$alkyl, a natural amino acid, $Ar^1$ carbonyl, $Ar^2C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl) amino$C_{1-6}$alkylcarbonyl, amino, $C_{1-6}$alkylamino, $C_{1-6}$alkylcarbonylamino, or a radical of formula —$Alk^2$—$OR^{13}$ or —$Alk^2$—$NR^{14}R^{15}$;

wherein $Alk^2$ is $C_{1-6}$alkanediyl;

$R^{13}$ is hydrogen, $C_{1-6}$alkyl, $C_{1-6}$alkylcarbonyl, hydroxy$C_{1-6}$alkyl, $Ar^1$ or $Ar^2C_{1-6}$alkyl;

$R^{14}$ is hydrogen, $C_{1-6}$alkyl, $Ar^1$ or $Ar^2C_{1-6}$alkyl;

$R^{15}$ is hydrogen, $C_{1-6}$alkyl, $C_{1-6}$alkylcarbonyl, $Ar^1$ or $Ar^2C_{1-6}$alkyl;

$R^{17}$ is hydrogen, halo, cyano, $C_{1-6}$alkyl, $C_{1-6}$alkyloxycarbonyl, $Ar^1$;

$R^{18}$ is hydrogen, $C_{1-6}$alkyl, $C_{1-6}$alkyloxy or halo;

$R^{19}$ is hydrogen or $C_{1-6}$alkyl;

$Ar^1$ is phenyl or phenyl substituted with $C_{1-6}$alkyl, hydroxy, amino, $C_{1-6}$alkyloxy or halo; and $Ar^2$ is phenyl or phenyl substituted with $C_{1-6}$alkyl, hydroxy, amino, $C_{1-6}$alkyloxy or halo, wherein said cancer is sensitive the effects of said farnesyl transferase inhibitor.

2. The method of claim 1 wherein the farnesyl protein transferase inhibitor is administered at a dose of 50–1200, mg/kg body weight.

3. The method of claim 1 wherein the farnesyl protein transferase inhibitor is administered at a dose of 50–400, mg/kg body weight.

4. The method of claim 1 wherein the farnesyl protein transferase inhibitor is administered at a dose of 50–200, mg/kg body weight.

5. The method of claim 1 wherein the farnesyl protein transferase inhibitor is administered for one day.

6. The method of claim 1 wherein the farnesyl protein transferase inhibitor is administered for five days.

7. The method of claim 1 wherein said farnesyl protein transferase inhibitor is a compound of formula (I) wherein X is oxygen and the dotted line represents a bond.

8. The method of claim 1 wherein said farnesyl protein transferase inhibitor is a compound of formula (I) wherein $R^1$ is hydrogen, $C_{1-6}$alkyl, $C_{1-6}$alkyloxy$C_{1-6}$alkyl or, mono- or di($C_{1-6}$alkyl)amino$C_{1-6}$alkyl;

$R^2$ is halo, $C_{1-6}$alkyl, $C_{2-6}$alkenyl, $C_{1-6}$alkyloxy, trihalomethoxy, or hydroxy$C_{1-6}$alkyloxy; and $R^3$ is hydrogen.

9. The method of claim 1 wherein $R^8$ is hydrogen, hydroxy, halo$C^{1-6}$alkyl, hydroxy$C^{1-6}$alkyl, cyano$C^{1-6}$alkyl, $C^{1-6}$alkyloxycarbonyl$C^{1-6}$alkyl, imidazolyl, or a radical of formula —$NR^{11}R^{12}$ wherein $R^{11}$ is hydrogen or $C_{1-12}$alkyl and $R^{12}$ is hydrogen, $C_{1-6}$alkyl, $C_{1-6}$alkyloxy, $C_{1-6}$alkyloxy$C_{1-6}$alkylcarbonyl, hydroxy, or a radical of formula —$Alk^2$—$OR^{13}$ wherein $R^{13}$ is hydrogen or $C_{1-6}$alkyl.

10. The method of claim 1 wherein the farnesyl protein transferase inhibitor is (+)-6-[amino(4-chlorophenyl)(1-methyl-1H-imidazol-5-yl)methyl]-4-(3-chlorophenyl)-1-methyl-2(1H)-quinolinone; or a pharmaceutically acceptable acid addition salt thereof.

* * * * *